United States Patent
Zeng et al.

(10) Patent No.: US 12,180,510 B2
(45) Date of Patent: **\*Dec. 31, 2024**

(54) METHODS AND COMPOSITIONS FOR RAPID GENERATION OF SINGLE AND MULTIPLEXED REPORTERS IN CELLS

(71) Applicant: RXCELL INC., Novato, CA (US)

(72) Inventors: Xianmin Zeng, Novato, CA (US); Mahendra S. Rao, Timonium, MD (US)

(73) Assignee: RxCell Inc., Novato, CA (US)

( * ) Notice: Subject to any disclaimer, the term of this patent is extended or adjusted under 35 U.S.C. 154(b) by 72 days.

This patent is subject to a terminal disclaimer.

(21) Appl. No.: 18/080,093

(22) Filed: Dec. 13, 2022

(65) Prior Publication Data

US 2023/0212524 A1 Jul. 6, 2023

Related U.S. Application Data

(62) Division of application No. 17/007,642, filed on Aug. 31, 2020, now Pat. No. 11,530,389, which is a division of application No. 15/536,340, filed as application No. PCT/US2015/064202 on Dec. 7, 2015, now Pat. No. 10,787,644.

(60) Provisional application No. 62/091,792, filed on Dec. 15, 2014.

(51) Int. Cl.
*C12N 15/90* (2006.01)
*C12N 5/074* (2010.01)

(52) U.S. Cl.
CPC ......... *C12N 5/0696* (2013.01); *C12N 15/907* (2013.01); *C12N 2510/00* (2013.01); *C12N 2750/14143* (2013.01); *C12N 2800/30* (2013.01); *C12N 2830/40* (2013.01); *C12N 2840/20* (2013.01)

(58) Field of Classification Search
CPC ................ C12N 5/0696; C12N 15/907; C12N 2510/00; C12N 2750/14143; C12N 2800/30; C12N 2830/40; C12N 2840/20
See application file for complete search history.

(56) References Cited

U.S. PATENT DOCUMENTS

| | | | | |
|---|---|---|---|---|
| 10,787,644 | B2 | 9/2020 | Zeng et al. | C12N 5/0696 |
| 11,530,389 | B2 | 12/2022 | Zeng et al. | 435/377 |
| 2009/0202988 | A1 | 8/2009 | Yamamura | 435/6 |
| 2009/0239305 | A1* | 9/2009 | Zhang | C12N 15/907 435/325 |
| 2011/0239319 | A1* | 9/2011 | Danos | C12N 9/22 435/320.1 |
| 2013/0274129 | A1* | 10/2013 | Katzen | C12N 15/1082 506/14 |
| 2016/0108369 | A1* | 4/2016 | Kuno | C12N 5/0696 435/366 |
| 2017/0145385 | A1* | 5/2017 | Prockop | C12N 5/0668 |

OTHER PUBLICATIONS

Gantz et al.(PLoS One Oct. 10, 2012, Voi7, No. 10, pp. e4691, 1-9; IDS ref) (Year: 2012).*
Du et al "Cre recombination-mediated cassette exchange for building versatile transgenic human embryonic stem cells lines" (Stem cells 2009 vol. 27: pp. 1032-1041) (Year: 2009).*
Zhu et al in "Baculoviral transduction facilitates TALEN-mediated targeted transgene integration and Cre/LoxP cassette exchange in human-induced pluripotent stem cells" (Nucleic Acids Research 2013 vol. 41, No. 19, pp. 1-12; published online Aug. 13, 2013 (Year : 2013).*
Araki et al in "Site-directed integration of the ere gene mediated by Cre recombinase using a combination of mutant lox sites" ( Nucleic Acids Research 2002 vol. 30, Vo. 19, pp. 1-8). (Year: 2002).*
Pei et al in "A platform for rapid generation of single and multi-plexed reporters in human iPSC lines" (Sci Rep 2015; vol. 5 ) (Year: 2015).*
Ananiev et al. "Isogenic pairs of wild type and mutant induced pluripotent stem cell (iPSC) lines from Rett syndrome patients as in vitro disease model." Plos one 2011 6:e25255.
Boch et al. "Breaking the code of DNA binding specificity of TAL-type III effectors" Science 2009 326:1509-1512.
Fu, X. & Xu, Y. "Challenges to the clinical application of pluripotent stem cells: towards genomic and functional stability" Genome medicine 2012 4:55.
Gantz et al. "Targeted genomic integration of a selectable floxed dual fluorescense reporter inm human embryonic stem cells" PLoS One Oct. 10, 2012 vol. 7 No. 10 pp. e4691 1-9.
Han et al. "Identification by Automated Screening of a Small Molecule that Selectively Eliminates Neural Stem Cells Derived from hESCs but Not Dopamine Neurons" PLoS One 2009 4:e7155.
Ho et al. "Current Applications of Human Pluripotent Stem Cells: Possibilities and Challenges" Cell transplantation 2012 21: 801-814.
Holkers et al. "Differential integrity of TALE nuclease genes following adenoviral and lentiviral vector gene transfer into human cells" Nucleic acids research 2013 41: e63.
Kumar et al. "Cellular manganese content is developmentally regulated in human dopaminergic neurons" Neurotoxicology 2012 33:518-529.
Laustriat et al. "Human pluripotent stem cells in drug discovery and predictive toxicology" Biochemical Society Transactions 2010 38: 1051-1057.
Luo et al. "Stable Enhanced Green Fluorescent Protein Expression After Differentiation and Transplantation of Reporter Human Induced Pluripotent Stem Cells Generated by AAVS1 Transcription Activator-Like Effector Nucleases" Stem Cells Translational Medicine 2014 3:821-835.
Maggio et al. "Adenoviral vector delivery of RNA-guided CRISPR/Cas9 nuclease complexes induces targeted mutagenesis in a diverse array of human cells" Scientific Reports 2014 4:5105.

(Continued)

*Primary Examiner* — Catherine S Hibbert
(74) *Attorney, Agent, or Firm* — Licata & Tyrrell P.C.

(57) ABSTRACT

Methods and compositions for rapid development of reporter lines utilizing safe harbor sites in iPSCS, as well as other progenitor cells, pluripotent and multipotent stem cells and differentiated cells, and multiple Lox sites are provided.

8 Claims, 10 Drawing Sheets

Specification includes a Sequence Listing.

(56) References Cited

OTHER PUBLICATIONS

Mali et al. "RNA-guided human genome engineering via Cas9" Science 2013 339:823-826.
Matsa et al. "Human Stem Cells for Modeling Heart Disease and for Drug Discovery" Science Translational Medicine 2014 6:239.
Moscou, M. J. & Bogdanove, A.J. "A simple cipher governs DNA recognition by TAL effectors." Science 2009 326:1501.
Peng et al. "Using human pluripotent stem cell-derived dopaminergic neurons to evaluate candidate Parkinson's disease therapeutic agents in MPP+ and rotenone models" Journal of Biomolecular Screening 2013 18:522-533.
Shtrichman et al. "Induced pluripotent stem cells (iPSCs) derived from different cell sources and their potential for regenerative and personalized medicine" Current Molecular Medicine 2013 13:792-805.
Sinnecker et al. "Modeling Long-QT Syndromes with iPS Cells" Journal of Cardiovascular Translational Research 2013 6:31-36.
Sinnecker et al. "Induced pluripotent stem cell-derived cardiomyocytes for drug development and toxicity testing" Pharmacology & Therapeutics 2014 143: 246-252.
Sun et al. "Future challenges for patient-specific induced pluripotent stem cells in cardiovascular medicine" Expert Review of Cardiovascular Therapy 2012 10: 943-945.
Tabar, V. & Studer, L. "Pluripotent stem cells in regenerative medicine: challenges and recent progress" Nature Reviews. Genetics 2014 15: 82-92.
Urnov et al. "Highly efficient endogenous human gene correction using designed zinc-finger nucleases" Nature 2005 435:646-651.
Vojnits, K. & Bremer, S. "Challenges of using pluripotent stem cells for safety assessments of substances" Toxicology 2010 270:10-17.
Wang et al. "Targeted gene addition to a predetermined site in the human genome using a ZFN-based nicking enzyme" Genome Research 2012 22:1316-1326.
International Search Report and Written Opinion in PCT/US2015/064202 dated Feb. 11, 2016.
International Preliminary Report on Patentability in PCT/US2015/064202 dated Jun. 20, 2017.
Araki et al. "Site-directed integration of the cre gene mediated by Cre recombinase using a combination of mutant lox sites" nucleic Acids Research 2002 30(19) :e103 pp. 1-8.
Du et al. "Cre Recombination Mediated Cassette Exchange For Building Versatile Transgenic Human ESC lines" Stem Cells 2009 27(5):1032-1041.
Zhu et al. "Baculoviral transduction facilitates TALEN-mediated targeted transgene integration and Cre/LoxP cassette exchange in human-induced pluripotent stem cells" Nucleic Acids Research 2013 41(19) :e180 pp. 1-12.
Office Communication dated Feb. 28, 2019 in U.S. Appl. No. 15/536,340, filed Jun. 15, 2017.
Office Communication dated Jul. 29, 2019 in U.S. Appl. No. 15/536,340, filed Jun. 15, 2017.
Office Communication dated Apr. 30, 2020 in U.S. Appl. No. 15/536,340, filed Jun. 15, 2017.
Office Communication dated Jun. 17, 2020 in U.S. Appl. No. 15/536,340, filed Jun. 15, 2017.
Office Communication dated Sep. 8, 2022 in U.S. Appl. No. 17/007,642, filed Aug. 31, 2020.
Pei et al. "A platform for rapid generation of single and multiplexed reporters in human iPSC lines" Scientific Reports 2015 5:9205 pp. 1-10.

* cited by examiner

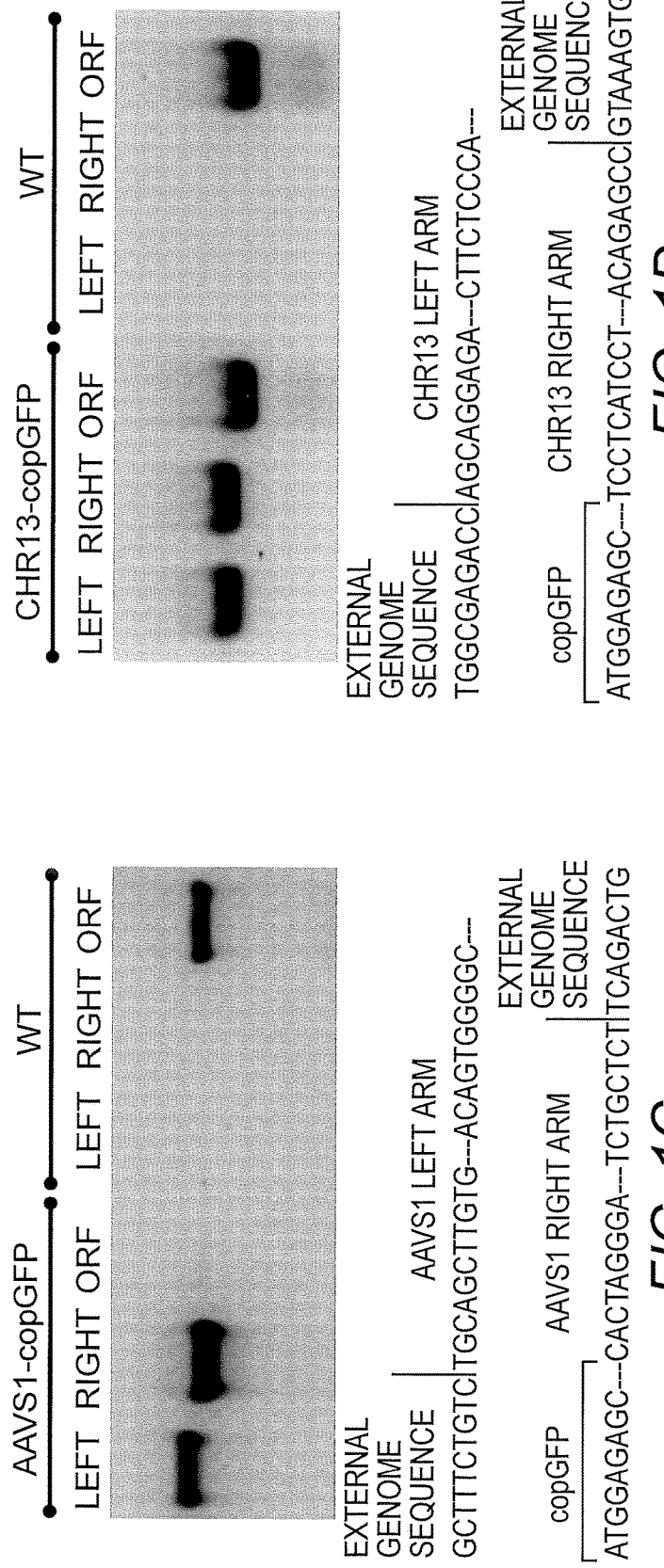
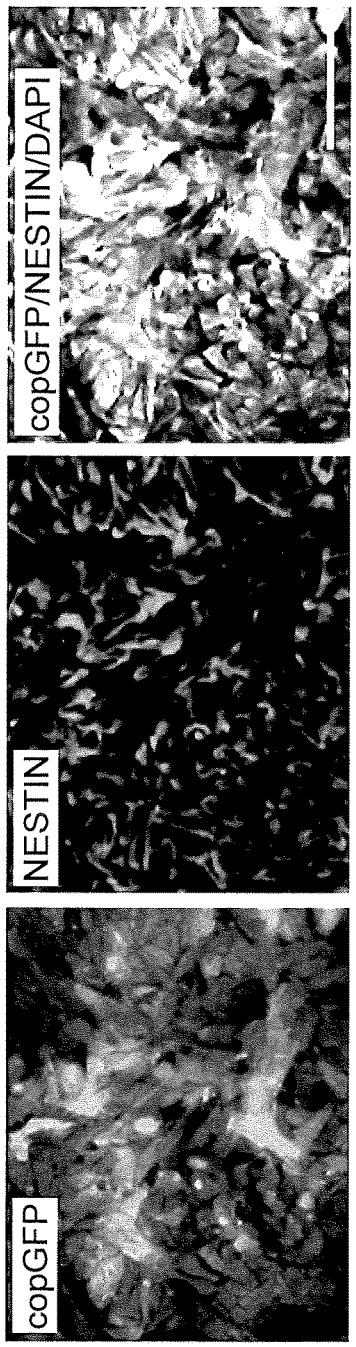
FIG. 1C
FIG. 1D
FIG. 1E

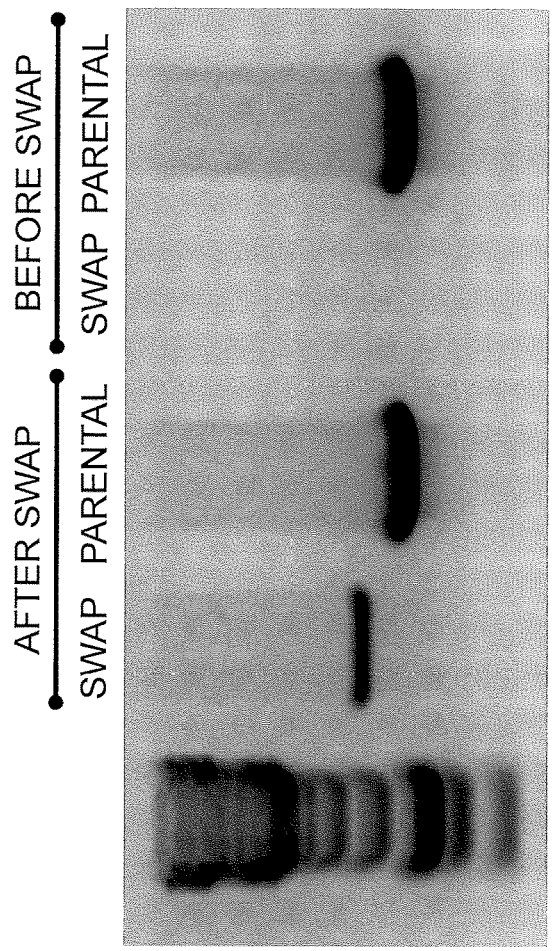
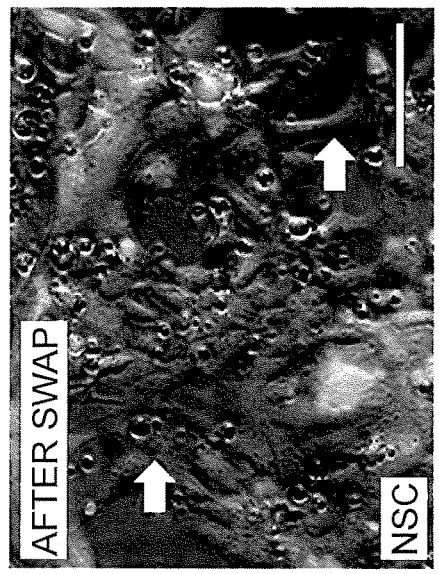
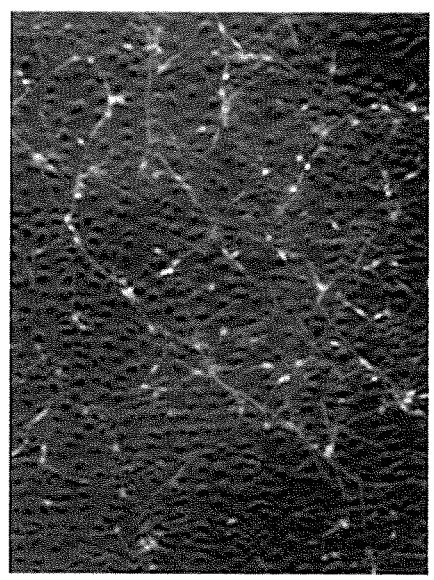
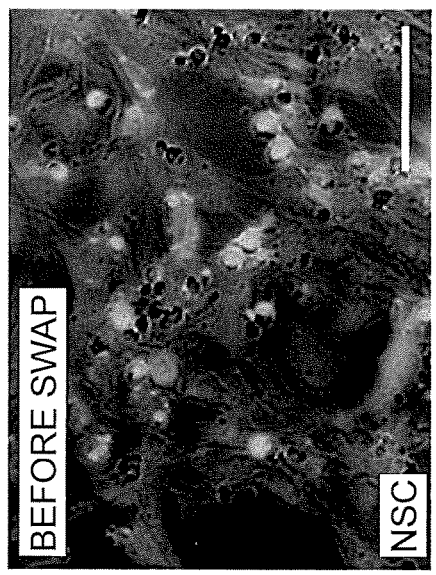
FIG. 2F
FIG. 2E
FIG. 2D

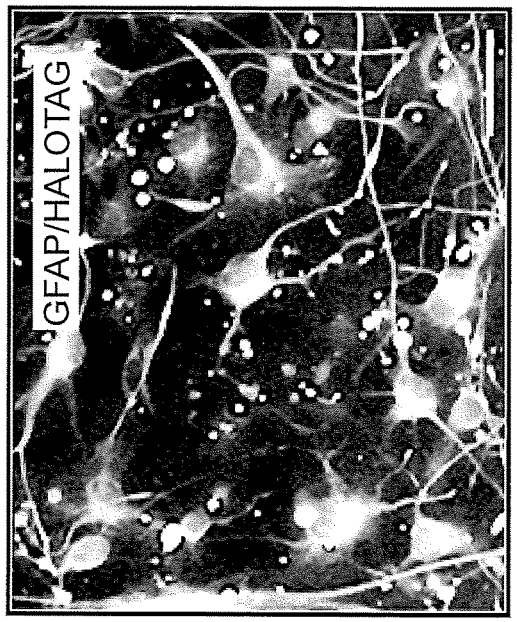
FIG. 4B
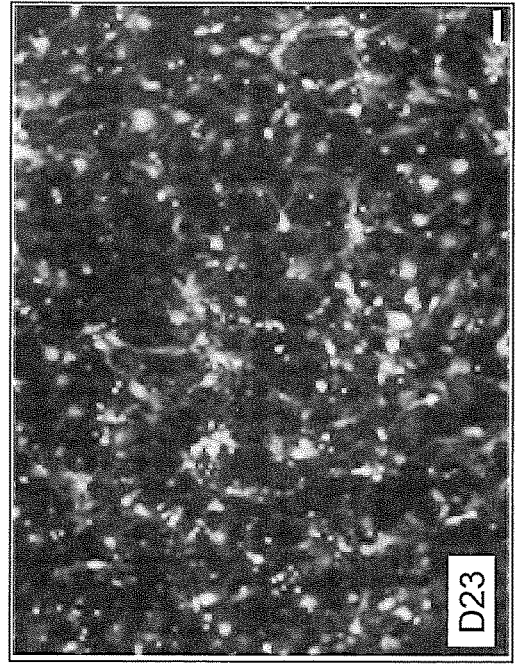
FIG. 4C
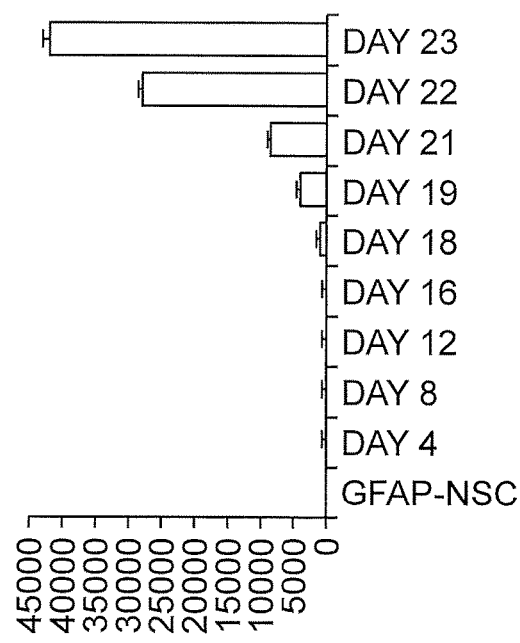
FIG. 4A
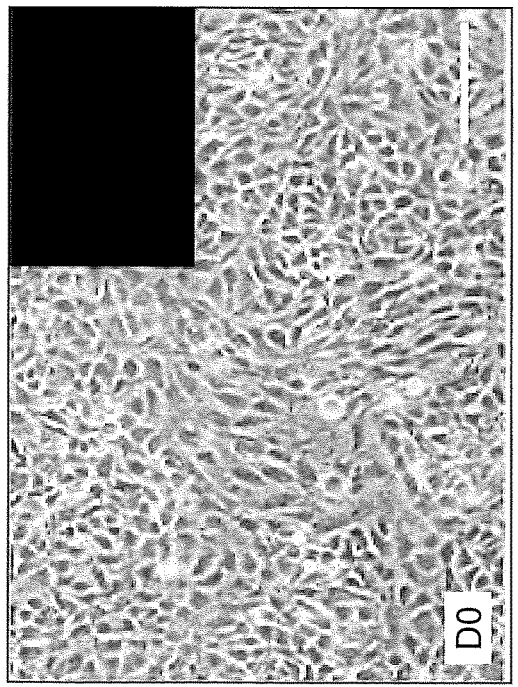

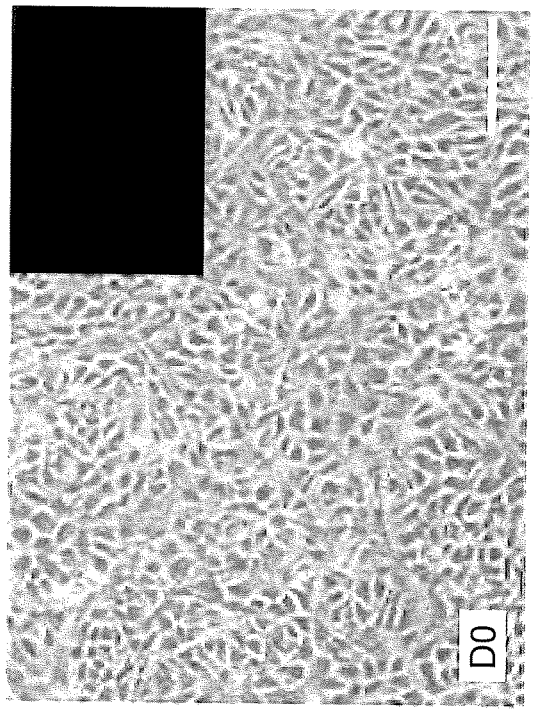
FIG. 4F
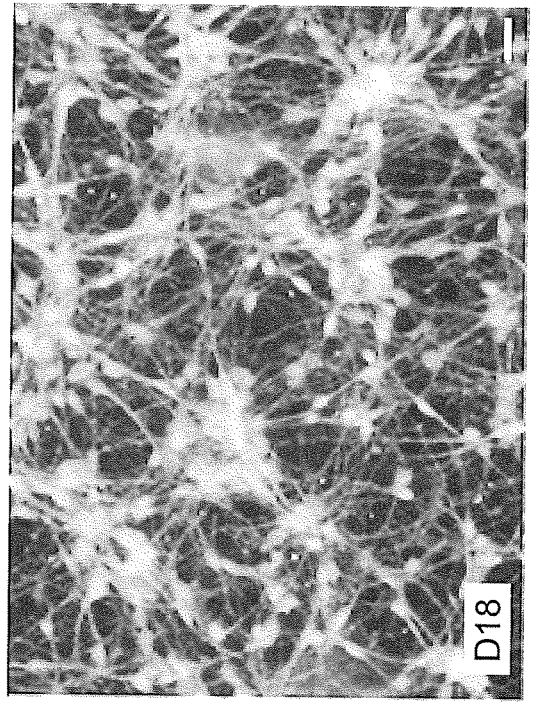
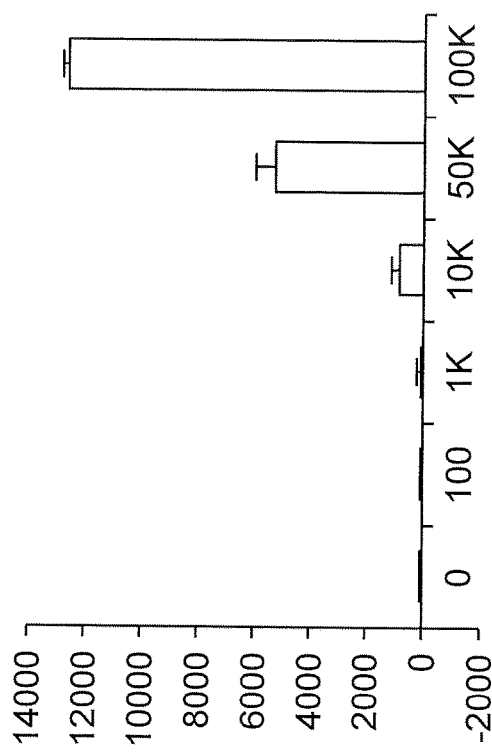
FIG. 4G
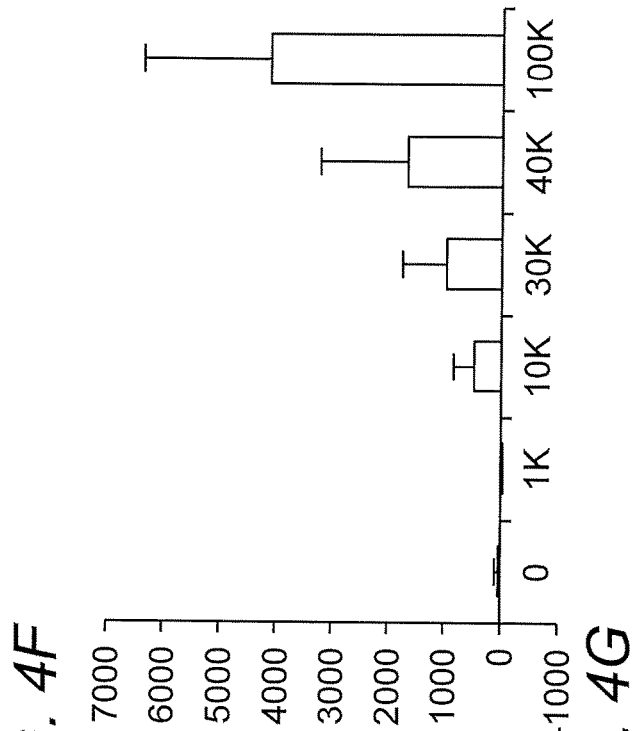

METHODS AND COMPOSITIONS FOR RAPID GENERATION OF SINGLE AND MULTIPLEXED REPORTERS IN CELLS

This patent application is a divisional of U.S. application Ser. No. 17/007,642, filed Aug. 31, 2020, which is a divisional of U.S. application Ser. No. 15/536,340, filed Jun. 15, 2017, which is the U.S. National Stage of PCT/US2015/064202, filed Dec. 7, 2015, which claims the benefit of priority from U.S. Provisional Application Ser. No. 62/091,792, filed Dec. 15, 2014, the contents of each of which are herein incorporated by reference in their entirety.

REFERENCE TO AN ELECTRONIC SEQUENCE LISTING

The contents of the electronic sequence listing (RXC0004USD2.xml); Size 54,000 bytes; and Date of Creation: Dec. 13, 2022) is herein incorporated by reference in its entirety.

FIELD OF THE INVENTION

The present invention relates to a method for rapid development of reporter lines utilizing safe harbor sites in iPSCS as well as other progenitor cells, pluripotent or multipotent stem cell, and differentiated cells. A master cell line which uses a Cre-recombinase induced cassette exchange strategy is also provided to rapidly exchange reporter cassettes to develop new reporter lines in the same isogenic background at high efficiency. Vector constructs used to generate these lines, as well as the selected promoters and reporters, can be multiplexed to provide ratio-metric measurements and quantitative analysis as well as monitoring lineage-specific differentiation in vitro and in vivo.

BACKGROUND

Induced pluripotent stem cells (iPSC) are rapidly becoming a mainstay of in vitro human cell-based assays for both toxicology and drug discovery. This has been possible due to a slew of advances in the field, which include techniques for high efficiency homologous recombination using transcription activator-like effector nuclease (TALEN), zinc finger nucleases (ZFN) or clustered regularly interspaced short palindromic repeats (CRISPRs)/cas9 system (Mali et al. Science 2013 339:823-826; Boch et al. Science 2009 326: 1509-1512; Urnov et al. Nature 2005 435:646-651; and Moscou, M. J. & Bogdanove, A. J. Science 2009 326:1501), and the ability to make integration-free iPSC cost effectively from normal individuals and patients with monogenic and polygenic diseases. Combined with advances in differentiating iPSC into multiple cell types, this allows the same signaling pathways or the same mutation to be assessed in a common allelic background. The power of this approach has been demonstrated by multiple groups using human cells rather than the standard xeno models used in the past (Han et al. PLoS One 2009 4:e7155; Matsa et al. Science translational medicine 2014 6:239; Peng et al. Journal of biomolecular screening 2013 18:522-533; Sinnecker et al. Journal of cardiovascular translational research 2013 6:31-36). Other groups have used iPSC-based models to identify patients who might adversely respond to an approved drug therapy or discover new drugs to treat a disease (Laustriat et al. Biochemical Society transactions 2010 38: 1051-1057; Sinnecker et al. Pharmacology & therapeutics 2014 143: 246-252; Shtrichman et al. Current molecular medicine 2013 13:792-805; Kumar et al. Neurotoxicology 2012 33:518-529; Ananiev et al. PloS one 2011 6:e25255).

Although these efforts clearly demonstrate the utility of using iPSC-derived cells for screening and toxicology assays, several issues have constrained the widespread use of such cells. Some of these issues include the time periods required to differentiate iPSC into an appropriate phenotype, the purity of the differentiated cells, and the consistency of the differentiation process. Further constraints include the lack of isogenic lines to control for allelic variability, the difficulty in generating reporter systems, and the time required to select stable subclones for assays (Vojnits, K. & Bremer, S. Toxicology 2010 270:10-17; Fu, X. & Xu, Y. Genome medicine 2012 4:55; Ho et al. Cell transplantation 2012 21: 801-814; Sun et al. Expert review of cardiovascular therapy 2012 10: 943-945; and Tabar, V. & Studer, L. Nature reviews. Genetics 2014 15: 82-92).

Several groups have begun to develop techniques to address these problems. For example researchers have shown that ZFN, TALEN and CRISPRs/cas9 systems provide efficient gene targeting technologies and allow one to develop safe harbor or lineage specific reporter system (Wang et al. Genome research 2012 22:1316-1326; Holkers et al. Nucleic acids research 2013 41: e63; Luo et al. Stem cells translational medicine 2014 3:821-835; Maggio et al. Scientific reports 2014 4:5105). It has also been shown that it is possible to make GFP and luciferase reporter lines using a standardized targeting system for safe harbor sites where expression is not silenced during differentiation (Luo et al. Stem cells translational medicine 2014 3:821-835).

SUMMARY OF THE INVENTION

An aspect of the present invention relates to a method for developing a master cell line. The method comprises integrating a reporter cassette into a cell at a safe harbor site. The reporter cassette comprises a reporter gene driven by a constitutively active promoter and multiple Lox sites.

Another aspect of the present invention relates to master cell line integrated with a reporter cassette at a safe harbor site in the cell. The reporter cassette comprises a reporter gene driven by a constitutively active promoter and multiple Lox sites.

Yet another aspect of the present invention relates to a method of generating a new reporter line using the master cell line of this invention. In the method a Cre-recombinase induced cassette exchange strategy is used to exchange the reporter cassette in the master cell line with a new reporter cassette, thereby generating a new reporter line with the same isogenic background.

BRIEF DESCRIPTION OF THE FIGURES

FIGS. 1A through 1E. Efficient targeting of Chr. 19 and Chr. 13 safe harbor loci. Experimental strategy of generating AAVS1-copGFP (FIG. 1A) and Chr13-copGFP (FIG. 1B) iPSC lines. Solid black triangles represent the loxP sites and triangles filled with diagonal lines represent Lox sites for RMCE. Testing primer sets for "Left" (Left arm integration test), "Right" (Right arm integration test) and "ORF" (WT ORF test) are also illustrated. FIG. 1C shows validation of AAVS1-copGFP heterozyte and homozygote clones by junction PCR (upper) and sequencing (lower) of external genome sequence (SEQ ID NO:22)—AAVS1 Left Arm (SEQ ID NO:23) and copGFP (SEQ ID NO:24)—AAVS1 Right Arm (SEQ ID NO:25)—external genome sequence (SEQ ID NO:26). FIG. 1D shows validation of Chr13- copGFP heterozygote clone by junction PCR (upper) and sequencing (lower) of external genome sequence (SEQ ID NO:27)—CRH13 Left Arm (SEQ ID NO:28) and copGFP (SEQ ID NO:24)—CHR13 Right Arm (SEQ ID NO:29)—external genome sequence (SEQ ID NO:30). FIG. 1E shows the copGFP reporter gene in AAVS-copGFP line was not silenced while differentiated into neural stem cells (NSCs). Nestin antibody was used to label the NSCs. The scale bar in FIG. 1E is 100 μm.

FIGS. 2A through 2F. Rapid exchanging of reporter cassettes in safe harbors in iPSC and progenitor cells using a master cell line strategy. FIG. 2A shows the experimental strategy of quick and efficient generation of a reporter line via RMCE strategy. The master line, AAVS1-copGFP, was co-transfected with the Cre expression vector and the targeting plasmid DCXp-TagGFP carrying a lox2272-DCX-promoter-TagGFP-PGK-Neo-lox511 cassette for RMCE with the master line. Cells with successfully targeted recombination were neomycin resistant and expressed TagGFP under the endogenous promoter of DCX instead of the constitutive CAG promoter which is seen in the master line. Testing primers, "swap" (indicating the successful RMCE event) and "parental" (detecting the parental gene which has no swap event) were also illustrated. Solid black triangles represent the LoxP sites and triangles filled with diagonal lines represent Lox sites for RMCE. After Neomycin selection, colonies with no copGFP signal were selected under fluorescent microscope (FIG. 2B). Because the copGFP was constitutively active in the master line, the cells before swap were all green fluorescent (left; FIG. 2B). After correct swap, the CAG promoter driven copGFP was replaced by DCX promoter driven TagGFP whose expression is off at the iPSC stage, and cells were no longer fluorescent (right; FIG. 2B). FIG. 2C shows PCR verification of the selected non-fluorescent colonies. No "parental" PCR products were detected in any of the selected colonies. FIG. 2D shows neuronal differentiation was induced on iPSC selected above and immunostaining showed positive co-localization of DCX AB and TagGFP, suggesting that the TagGFP is only expressed when the DCX gene is turned on. RMCE strategy was also tested in the progenitor stage (NSC; FIG. 2E). AAVS1-copGFP master line NSC were co-transfected with Cre expressing vector and the targeting plasmid DCXp-TagGFP as described in (FIG. 2A). Before transfection, all AAVS1-copGFP NSC were green fluorescent (left; FIG. 2E). After 5 days post transfection, cells lost green fluorescence were detected under microscope (spots pointed by arrows in the right graph; FIG. 2E). FIG. 2F shows PCR verification of successful swapping event happened in NSC. Only "parental" PCR band was detectable in NSC before transfection. After RMCE, both "swap" and "parental" PCR products were detected in the mixed culture. Scale bar is 100 μm in FIGS. 2C and 2E.

FIG. 3A shows the experimental strategy of generating MAP2-Nanoluc-KI® (assay reagent for bioluminescence, Promega Corporation, WI). The designed ZFNs cut at the C-term of MAP2 gene before the stop codon. The left and right arms of MAP2 for homologous recombination were designed to be ~1 kb located before and after the stop codon, respectively. Testing primer sets for "Left" (MAP2 Left arm integration test), "Right" (MAP2 Right arm integration test) and "ORF" (WT MAP2 ORF test) are also illustrated. FIG. 3B shows the experimental strategy of generating GFAP-Nanoluc®-KI. The designed ZFNs cut after the stop codon of GFAP ORF. The left and right arms of GFAP for homologous recombination were designed to be ~1 kb located before and after the stop codon, respectively. Testing primer sets for "Left" (GFAP Left arm integration test), "Right" (GFAP Right arm integration test) and "ORF" (WT GFAP ORF test) are also illustrated. FIG. 3C shows validation of MAP2-Nanoluc®-KI clone by junction PCR (upper) and sequencing (lower) of external genome sequence (SEQ ID NO:31)—MAP2 Left Arm with P2A (SEQ ID NO:32) and P2A Nanoluc® (SEQ ID NO:33)—MAP2 Right Arm (SEQ ID NO:34)—external genome sequence (SEQ ID NO:35). FIG. 3D shows validation of GFAP-Nanoluc®-KI clone by junction PCR (upper) and sequencing (lower) of external genome sequence (SEQ ID NO:36)—GFAP Left Arm with P2A (SEQ ID NOL37) and P2A with Nanoluc® (SEQ ID NO: 33)—GFAP Right Arm (SEQ ID NO:38)—external genome sequence (SEQ ID NO:39).

FIGS. 4A through 4G: Functional validation of lineage-specific expression. FIG. 4A as is a bar graph showing an increase of luciferase level in culture media detected in the GFAP-Nanoluc®-KI cell lines during directed differentiation into astrocytes. Luciferase levels shown in the bar graph were normalized by the basal level detected at day 0 in GFAP-Nanoluc®-KI NSC. Immunostaining showed excellent co-localization of HaloTag® (reagent for production, tagging capturing or immobilizing of fusion proteins from solutions or extracts; Promega Corporation, WI) and GFAP antibodies in the GFAP-Nanoluc®-KI astrocytes (D23 post differentiation; FIG. 4B). Live staining of HaloTag® in the GFAP-Nanoluc®-KI cell line before (left) and after (right) directed differentiation into astrocytes as shown in FIG. 4C. As shown in FIG. 4D, an increase of luciferase level in culture media was detected in the MAP2-Nanoluc®-KI cell lines during directed differentiation into neurons. Luciferase levels shown in the bar graph were normalized by the basal level detected at day 0 in the MAP2-Nanoluc®-KI NSC. Immunostaining showed excellent co-localization of HaloTag® and MAP2 antibodies in the MAP2-Nanoluc®-KI neurons (D18 post differentiation; FIG. 4E). Live staining of HaloTag® in the MAP2-Nanoluc®-KI cell line before (left; FIG. 4F) and after (right; FIG. 4F) directed differentiation into neurons. A series dilution of GFAP-Nanoluc®-KI (left; FIG. 4G) and MAP2-Nanoluc®-KI (right; FIG. 4G) iPSC were plated and luciferase level from the media was tested. The minimum cell amount needed was 10K for detectable luciferase level of both GFAP-Nanoluc®-KI and MAP2-Nanoluc®-KI iPSC lines. Scale bars shown in FIGS. 4B, 4C, 4E and 4F are all 100 μm.

SEQUENCE LISTING

Figures 1A, 1B:
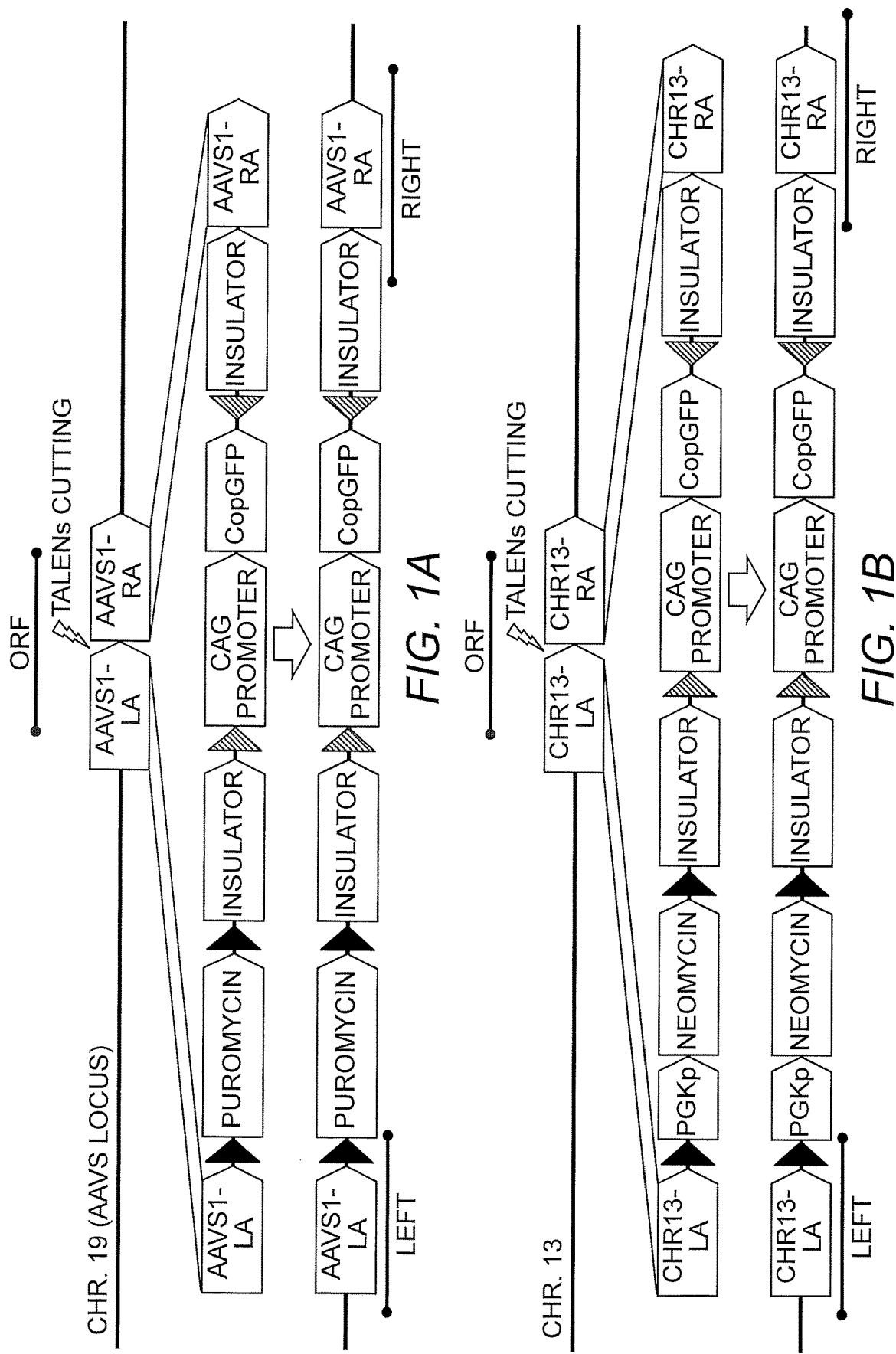

The nucleic and amino acid sequences disclosed herein use standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. Sequence names for SEQ ID NOs 1-21 as set forth in the Sequence Listing provided herewith are as follows:

| SEQ ID NO: | Sequence name |
|---|---|
| 1 | Upstream CLYBL target |
| 2 | Upstream CLYBL TALE binding domain |
| 3 | Downstream CLYBL target |
| 4 | Downstream CLYBL TALE binding domain |
| 5 | Upstream TALEN - Includes Δ152 N-terminus and +63 C-terminus |
| 6 | Downstream TALEN - Includes Δ152 N-terminus and +63 C-terminus |
| 7 | Upstream CLYBL TALE binding domain |
| 8 | Upstream TALEN - Includes Δ152 N-terminus and +63 C-terminus |
| 9 | pZT-C13-L |
| 10 | Downstream CLYBL TALE binding domain |
| 11 | Downstream TALEN - Includes Δ152 N-terminus and +63 C-terminus |
| 12 | pZT-C13-R |
| 13 | FokI Nuclease |
| 14 | FokI Nuclease |
| 15 | Nuclear localization signal |
| 16 | Nuclear localization signal |
| 17 | FLAG tag |
| 18 | FLAG tag |
| 19 | CLYBL target region |
| 20 | Primer |
| 21 | Primer |

DETAILED DESCRIPTION OF THE INVENTION

Induced pluripotent stem cells (iPSC) are important tools for drug discovery assays and toxicology screens. The present invention provides a unique platform for rapidly developing custom single or dual reporter systems for screening assays in iPSCs, other progenitor cells, pluripotent and multipotent stem cells and differentiated cells.

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Cell Culture: Cells grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Differentiation: The process whereby relatively unspecialized cells (e.g., embryonic cells or stem cells) acquire specialized structural and/or functional features characteristic of mature cells. Similarly, "differentiate" refers to this process. Typically, during differentiation, cellular structure alters and tissue-specific proteins and properties appear.

Differentiation medium: A synthetic set of culture conditions with the nutrients necessary to support the growth or survival of microorganisms or culture cells, and which allows the differentiation of cells, such as mesenchymal stem cells.

Donor polynucleotide: A polynucleotide that is capable of specifically inserting into a genomic locus.

Downstream: A relative position on a polynucleotide, wherein the "downstream" position is closer to the 3' end of the polynucleotide than the reference point. In the instance of a double-stranded polynucleotide, the orientation of 5' and 3' ends are based on the sense strand, as opposed to the antisense strand.

Embryonic Stem (ES) Cells: Pluripotent cells isolated from the inner cell mass of the developing blastocyst, or the progeny of these cells. "ES cells" can be derived from any organism. ES cells can be derived from mammals, including mice, rats, rabbits, guinea pigs, goats, pigs, cows, monkeys and humans. In specific, non-limiting examples, the cells are human or murine. Without being bound by theory, ES cells can generate a variety of the cells present in the body (bone, muscle, brain cells, etc.), provided they are exposed to conditions conducive to developing these cell types. Methods for producing murine ES cells can be found in U.S. Pat. No. 5,670,372, which is herein incorporated by reference. Methods for producing human ES cells can be found in U.S. Pat. No. 6,090,622, WO 00/70021 and WO 00/27995, which are herein incorporated by reference.

Effective amount or Therapeutically effective amount: The amount of agent, such a cell, for example MSCs, that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount sufficient to reduce or eliminate a symptom of a disease. In another embodiment, a therapeutically effective amount is an amount sufficient to overcome the disease itself.

Exogenous: Not normally present in a cell, but can be introduced by genetic, biochemical or other methods. Exogenous nucleic acids include DNA and RNA, which can be single or double-stranded; linear, branched or circular; and can be of any length. By contrast, an "endogenous" molecule is one that is normally present in a particular cell at a particular developmental stage under particular environmental conditions.

Expand: A process by which the number or amount of cells in a culture is increased due to cell division. Similarly, the terms "expansion" or "expanded" refers to this process.

The terms "proliferate," "proliferation" or "proliferated" may be used interchangeably with the words "expand," "expansion" or "expanded." Typically, during an expansion phase, the cells do not differentiate to form mature cells.

Expansion medium: A synthetic set of culture conditions suitable for the expansion of cells, such as mesenchymal stem cells. Tissue culture media generally include a carbon source, a nitrogen source and a buffer to maintain pH. In one embodiment, a medium contains a minimal essential media, such as DMEM, supplemented with various nutrients to enhance mesenchymal stem cell growth.

Additionally, the minimal essential media may be supplemented with additives such as horse, calf or fetal bovine serum.

FokI nuclease: A nonspecific DNA nuclease that occurs naturally in *Flavobacterium okeanokoites*. The term includes fragments of the FokI nuclease protein that retain nuclease activity that are, or may be, fused to a DNA-binding polypeptide.

Genomic insertion site: A site of the genome that is targeted for, or has undergone, insertion of an exogenous polynucleotide.

Growth factor: A substance that promotes cell growth, survival, and/or differentiation. Growth factors include molecules that function as growth stimulators (mitogens), molecules that function as growth inhibitors (e.g. negative growth factors) factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are bFGF, epidermal growth factor (EGF), CNTF, HGF, nerve growth factor (NGF), and actvin-A.

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Induced pluripotent stem cell" ("iPS" cell or "iPSC"): A pluripotent stem cell artificially derived from a non-pluripotent cell, typically an adult somatic cell, by recombinant expression of specific factors in the non-pluripotent cell. Factors that may be used to for iPSCs include, but are not limited to, one or more of Oct-3/4, certain members of the Sox gene family (Sox1, Sox2, Sox3, and Sox15, Klf family members (Klf1, Klf2, Klf4, and Klf5), factors of the Myc family (c-myc, L-myc, and N-myc), Nanog, and LIN28, as defined by current knowledge in the art. Other factors or methods useful for creating iPSCs are also known in the art and are considered to produce cells that fall within the scope of this definition.

Isolated: An "isolated" biological component (such as a nucleic acid, peptide or cell) has been substantially separated, produced apart from, or purified away from other biological components or cells of the organism in which the component naturally occurs, i.e., other chromosomal and extrachromosomal DNA and RNA, cells and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Lineage-specific: Characteristics of a cell that indicate the cell will become one of a limited number of related cell types or a particular cell type, such as a differentiated cell or a cell undergoing the process of differentiation into a specific cell type or a mature cell type.

Mesenchymal Stem Cell (MSC): Also referred to as multipotent stromal cells and meant to be inclusive not only of MSCs but also of cells with replicative potential similar thereto that can differentiate into a variety of cell types. Additional examples of cells meant to be encompassed herein by the terms MSC and/or mesenchymal stem cells include, but are not limited to, mesenchymal precursor cells or MPCs, mesenchymal progenitor cells such as described by Mesoblast, Ltd., and other adult-derived stem cells such as MULTISTEM (Athersys, Inc.). While these multipotent stem cells are traditionally found in the bone marrow, they can also be isolated from other tissues including, but not limited to, cord blood, peripheral blood, fallopian tube, fetal liver and lung, placenta and fat. MSCs and other adult stem cells which can be used in accordance with the present invention, differentiate to form cells and/or tissues including, but not limited, adipocytes, cartilage, bone, tendons, muscle, and skin as well as myocytes, neurons and glia.

Modulate: A change in the content of genomic DNA gene. Modulation can include, but is not limited to, gene activation, gene repression, gene deletion, polynucleotide insertion, and polynucleotide excision.

Neural cell: A cell that exhibits a morphology, a function, and a phenotypic characteristic similar to that of glial cells and neurons derived from the central nervous system and/or the peripheral nervous system.

There are several types of neurons (neuronal cells). Cholinergic neurons manufacture acetylcholine. GABAergic neurons manufacture gamma aminobutyric acid (GABA). Glutamatergic neurons manufacture glutamate. Dopaminergic neurons manufacture dopamine. Serotonergic neurons manufacture serotonin.

Neuronal stem cell or neural stem cell (NSC): Undifferentiated, multipotent, self-renewing neural cell. A NSC is a multipotent stem cell which is able to divide and, under appropriate conditions, has self-renewal capability and can terminally differentiate into neurons, astrocytes, and oligodendrocytes. Hence, the neural stem cell is "multipotent" because stem cell progeny have multiple differentiation pathways. A NSC is capable of self maintenance, meaning that with each cell division, at least one daughter cell will also be, on average, a stem cell. Neural stem cells can be derived from tissues including, but not limited to brain and spinal cord. A "long term" NSC divides in culture for at least 15 cell divisions, such as at least 15, 20, 25, 30, 35, 40, 45 or 50 cell divisions. A long term retains the properties of a neuronal stem cell, such as expression of nestin and sox1, and has the capacity to differentiate into neurons and glia in appropriate culture conditions in vitro.

NSCs can be obtained from a cadaver or living subject, including from fetal tissue and adult brain biopsies. NSCs can be produced from other stem cells, such as induced pluripotent stem cells or embryonic stem cells. NSCs can be autologous or heterologous to a recipient.

Neurological disorder: A disorder in the nervous system, including the central nervous system (CNS) and peripheral nervous system (PNS). Examples of neurological disorders include Parkinson's disease, Huntington's disease, Alzheimer's disease, severe seizure disorders including epilepsy, familial dysautonomia as well as injury or trauma to the nervous system, such as neurotoxic injury or disorders of mood and behavior such as addiction, schizophrenia and amyotrophic lateral sclerosis. Neuronal disorders also include Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and other lipid storage and genetic brain diseases and/or schizophrenia Neurodegenerative disorder: An abnormality in the nervous system of a subject, such as a mammal, in which neuronal integrity is threatened. Without being bound by theory, neuronal integrity can be threatened when neuronal cells display decreased survival or when the neurons can no longer propagate a signal. Specific, non-limiting examples of a neurodegenerative disorder are Alzheimer's disease, Pantothenate kinase associated neurodegeneration, Parkinson's disease, Huntington's disease (Dexter et al., *Brain* 114:1953-1975, 1991), HIV encephalopathy (Miszkziel et al., *Magnetic Res. Imag.* 15:1113-1119, 1997), and amyotrophic lateral sclerosis.

Alzheimer's disease manifests itself as pre-senile dementia. The disease is characterized by confusion, memory failure, disorientation, restlessness, speech disturbances, and hallucination in mammals (*Medical, Nursing, and Allied Health Dictionary*, 4th Ed., 1994, Editors: Anderson, Anderson, Glanze, St. Louis, Mosby).

Parkinson's disease is a slowly progressive, degenerative, neurologic disorder characterized by resting tremor, loss of postural reflexes, and muscle rigidity and weakness (*Medical, Nursing, and Allied Health Dictionary*, 4th Ed., 1994, Editors: Anderson, Anderson, Glanze, St. Louis, Mosby).

Amyotrophic lateral sclerosis is a degenerative disease of the motor neurons characterized by weakness and atrophy of the muscles of the hands, forearms and legs, spreading to involve most of the body and face (*Medical, Nursing, and Allied Health Dictionary*, 4th Ed., 1994, Editors: Anderson, Anderson, Glanze, St. Louis, Mosby).

Pantothenate kinase associated neurodegeneration (PKAN, also known as Hallervorden-Spatz syndrome) is an autosomal recessive neurodegenerative disorder associated with brain iron accumulation. Clinical features include extrapyramidal dysfunction, onset in childhood, and a relentlessly progressive course (Dooling et al., *Arch. Neurol.* 30:70-83, 1974). PKAN is a clinically heterogeneous group of disorders that includes classical disease with onset in the first two decades, dystonia, high globus pallidus iron with a characteristic radiographic appearance (Angelini et al., *J. Neurol.* 239:417-425, 1992), and often either pigmentary retinopathy or optic atrophy (Dooling et al., *Arch. Neurol.* 30:70-83, 1974; Swaiman et al., *Arch. Neurol* 48:1285-1293, 1991).

A "neurodegenerative-related disorder" is a disorder such as speech disorders that are associated with a neurodegenerative disorder. Specific non-limiting examples of a neurodegenerative related disorders include, but are not limited to, palilalia, tachylalia, echolalia, gait disturbance, perseverative movements, bradykinesia, spasticity, rigidity, retinopathy, optic atrophy, dysarthria, and dementia.

Nucleofection: Electroporation. Nucleofection uses a combination of electrical parameters, generated by a device called Nucleofector, with cell-type specific reagents. The substrate is transferred directly into the cell nucleus and the cytoplasm.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent or "drug": A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Polypeptide: Three or more covalently attached amino acids. The term encompasses proteins, protein fragments, and protein domains. A "DNA-binding" polypeptide is a polypeptide with the ability to specifically bind DNA.

The term "polypeptide" is specifically intended to cover naturally occurring proteins, as well as those which are recombinantly or synthetically produced. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Recombination: A process of exchange of genetic information between two polynucleotides. "Homologous recombination (HR)" refers to the specialized form of an exchange that takes place, for example, during repair of double-strand breaks in cells. Nucleotide sequence homology is utilized in recombination, for example using a "donor" molecule to template repair of a "target" molecule (i.e., the one that experienced the double-strand break), and is variously known as "non-crossover gene conversion" or "short tract gene conversion," because it leads to the transfer of genetic information from the donor to the target.

Safe harbor: A locus in the genome where a polynucleotide may be inserted without causing deleterious effects to the host cell. Examples of safe harbor loci known to exist within mammalian cells may be found within the AAVS1 gene, the CYBL gene, and the CCR5 gene.

Selectable marker: A gene introduced into a cell, such mammalian cells in culture, for example a MSC, that confers a trait suitable for artificial selection from cells that do not possess the gene.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a FGF polypeptide will possess a relatively high degree of sequence identity when aligned using standard methods.

Methods of alignment of sequences for comparison are well known in the art. Various programs and alignment algorithms are described in Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul, et al., *Nature Genet.*, 6:119, 1994 presents a detailed consideration of sequence alignment methods and homology calculations.

The NCBI Basic Local Alignment Search Tool (BLAST) (Altschul, et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a FGF polypeptide are typically characterized by possession of at least about 75%, for example at least about 80%, sequence identity counted over the full length alignment with the amino acid sequence of the factor using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding: A sequence-specific, non-covalent interaction between macromolecules (e.g., between a polypeptide and a polynucleotide). Not all components of a binding interaction need be sequence-specific (e.g., contacts with phosphate residues in a DNA backbone), as long as the interaction as a whole is sequence-specific. The term should not be construed to indicate that a macromolecule described as participating in specific binding, or as being specific for another given macromolecule, cannot bind to another macromolecule, but rather that the specific nature of the interaction is significantly favored over a nonspecific or random binding. Such "specific binding" interactions are generally characterized by a dissociation constant ($K_d$) of $10^{-6}$ $M^{-1}$ or lower.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human.

Synapse: Highly specialized intercellular junctions between neurons and between neurons and effector cells across which a nerve impulse is conducted (synaptically active). Generally, the nerve impulse is conducted by the release from one neuron (presynaptic neuron) of a chemical transmitter (such as dopamine or serotonin) which diffuses across the narrow intercellular space to the other neuron or effector cell (post-synaptic neuron). Generally neurotransmitters mediate their effects by interacting with specific receptors incorporated in the post-synaptic cell. "Synaptically active" refers to cells (e.g., differentiated neurons) which receive and transmit action potentials characteristic of mature neurons.

Transduced, Transformed and Transfected: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses (Wolff, J. A., ed, *Gene Therapeutics*, Birkhauser, Boston, USA, 1994). In the case of infection by retroviruses, the infecting retrovirus particles are absorbed by the target cells, resulting in reverse transcription of the retroviral RNA genome and integration of the resulting provirus into the cellular DNA. Methods for the introduction of genes into cells are known (e.g. see U.S. Pat. No. 6,110,743, herein incorporated by reference). These methods can be used to transduce a MSC or a cell produced by the methods described herein.

Genetic modification of the target cell is an indicium of successful transfection. "Genetically modified cells" refers to cells whose genotypes have been altered as a result of cellular uptakes of exogenous nucleotide sequence by transfection. A reference to a transfected cell or a genetically modified cell includes both the particular cell into which a vector or polynucleotide is introduced and progeny of that cell.

Transgene: An exogenous gene.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

Upstream: A relative position on a polynucleotide, wherein the "upstream" position is closer to the 5' end of the polynucleotide than the reference point. In the instance of a double-stranded polynucleotide, the orientation of 5' and 3' ends are based on the sense strand, as opposed to the antisense strand.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Zinc finger DNA binding domain: A polypeptide domain that binds DNA in a sequence-specific manner through one or more zinc fingers, which are regions of amino acid sequence within the binding domain whose structure is stabilized through coordination of a zinc ion.

Zinc finger binding domains, for example the recognition helix of a zinc finger, can be "engineered" to bind to a predetermined nucleotide sequence. Rational criteria for design of zinc finger binding domains include application of substitution rules and computerized algorithms for processing information in a database storing information of existing ZFP designs and binding data, see for example U.S. Pat. Nos. 5,789,538; 5,925,523; 6,007,988; 6,013,453; 6,140,081; 6,200,759; 6,453,242; and 6,534,261; and PCT Publication Nos. WO 95/19431; WO 96/06166; WO 98/53057; WO 98/53058; WO 98/53059; WO 98/53060; WO 98/54311; WO 00/27878; WO 01/60970; WO 01/88197; WO 02/016536; WO 02/099084 and WO 03/016496.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, "A or B" is intended to include "A," "B," and "both A and B," unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods and Compositions for Rapid Generation of Single and Multiplexed Reporters in Cells An important feature of iPSCs is that they can be engineered in multiple ways to be used for screenings, for developing therapeutic purposes, or for investigating disease mechanisms or processes. For instance, iPSCs can be engineered to create ubiquitous reporters to develop enhanced assays, lineage-specific reporters to allow for stage-specific screening, or pathway and organelle reporters to allow for focused screening.

Disclosed herein are compositions and methods for rapid generation of single and multiplexed reporters in various iPSC cell lines as well as other progenitor cells including other pluripotent and multipotent stem cells and differentiated cells.

Efficient Targeting of Chr. 19 and Chr. 13 Safe Harbor Loci in Multiple Lines with Multiple Constructs High efficiency TALEN and ZEN were designed which target two safe harbor sites on chromosome 13 and 19 in an iPSC line.

Recombinant polynucleotide-binding polypeptides for use in targeting these chromosomes can occur in a variety of forms. In some embodiments, the recombinant polynucleotide-binding polypeptide is a recombinant DNA-binding polypeptide that specifically binds to a genomic target sequence in the cell. In one embodiment the targeted genomic sequence bound by the recombinant DNA-binding polypeptide falls within the sequence of SEQ ID NO: 19, or its corresponding antisense sequence. In another embodiment the targeted sequence bound by the recombinant DNA-binding polypeptide in the genome of the cell includes the sequence of SEQ ID NO: 1. In yet another embodiment, the targeted sequence bound by the recombinant DNA-binding polypeptide is the sequence of SEQ ID NO: 1. Alternatively, the targeted sequence bound by the recombinant DNA-binding polypeptide may include a sequence that is antisense, or complementary, to the sequence of SEQ ID NO: 1. In one embodiment, the targeted sequence bound by the recombinant DNA-binding polypeptide is a sequence that is antisense, or complementary, to the sequence of SEQ ID NO: 1. In another embodiment the targeted sequence bound by the recombinant DNA-binding polypeptide includes the sequence of SEQ ID NO: 3. In a further embodiment, the targeted sequence bound by the recombinant DNA-binding polypeptide is the sequence of SEQ ID NO: 3. Alternatively, the targeted sequence bound by the recombinant DNA-binding polypeptide can include a sequence that is antisense, or complementary, to the sequence of SEQ ID NO: 3. In one embodiment, the targeted sequence bound by the recombinant DNA-binding polypeptide is a sequence that is antisense, or complementary, to the sequence of SEQ ID NO: 3.

In some embodiments the described recombinant DNA-binding polypeptide includes a zinc-finger domain or a transcription activator-like effector (TALE) domain, or a polypeptide fragment thereof that retains the DNA binding function of the TALE domain or the zinc-finger domain. Furthermore, the recombinant DNA-binding polypeptide may also be combined with a polypeptide having nuclease activity, such as a zinc-finger domain or a transcription activator-like effector (TALE) domain fused to a nuclease protein, or a fragment thereof. Exemplary nucleases include, but are not limited to, S1 nuclease, mung bean nuclease, pancreatic DNAase I, micrococcal nuclease, and yeast HO endonuclease (see also Linn et al. (eds.) Nucleases, Cold Spring Harbor Laboratory Press, 1993).

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at nine nucleotides from its recognition site on one strand and 13 nucleotides from its recognition site on the other (see, for example, U.S. Pat. Nos. 5,356,802; 5,436,150 and 5,487,994; Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31, 978-31, 982). Thus, in one embodiment, a nuclease domain from at least one Type IIS restriction enzyme is utilized. An exemplary Type IIS restriction enzyme, whose cleavage domain is separable from the binding domain, is Fok1. This particular enzyme is active as a dimer. See Bitinaite et al. (1998) Proc. Natl. Acad. Sci. USA 95: 10, 570-10,575. Additional forms of FokI nuclease are set forth in U.S. Published Patent Application No. 20110027235, which is incorporated herein by reference.

In some embodiments the polypeptide having nuclease activity that is fused with the recombinant DNA-binding polypeptide is the FokI nuclease, or a derivative or fragment thereof that retains the nuclease activity. In some embodiments, the Fok1 nuclease is at least about 80%, at least about 85%, at least about 90%, at least about 95%, at least about 96%, at least about 97%, at least about 98%, at least about 99%, or about 100% identical to SEQ ID NO: 13.

In the case of a recombinant DNA-binding polypeptide produced from a TALE domain, fusion with a polypeptide having nuclease activity forms a transcription activator-like effector nuclease (TALEN). Some of the TALEN embodiments described herein are designed to specifically target a genomic sequence that falls within the sequence of SEQ ID NO: 19, or its corresponding antisense sequence, such as, for example, the sequence of SEQ ID NO: 1 or 3. In one embodiment the targeted sequence bound by a described TALE domain includes the sequence of SEQ ID NO: 1. In one embodiment, the targeted sequence bound by a described TALE domain is the sequence of SEQ ID NO: 1. Alternatively, the targeted sequence bound by a described TALE domain may include a sequence that is antisense, or complementary, to the sequence of SEQ ID NO: 1. In one embodiment, the targeted sequence bound by a described TALE domain is a sequence that is antisense, or complementary, to the sequence of SEQ ID NO: 1. In another embodiment the targeted sequence bound by a described TALE domain includes the sequence of SEQ ID NO: 3. In one embodiment, the targeted sequence bound by a described TALE domain is the sequence of SEQ ID NO: 3. Alternatively, the targeted sequence bound by a described TALE domain may include a sequence that is antisense, or complementary, to the sequence of SEQ ID NO: 3. In one embodiment, the targeted sequence bound by a described TALE domain is a sequence that is antisense, or complementary, to the sequence of SEQ ID NO: 3.

The TALE domains of use in the methods disclosed herein can be linked to a polypeptide having nuclease activity to form a TALEN, which can be used to cleave DNA at a specific location of interest. In one embodiment the targeted sequence bound by a described TALEN includes the sequence of SEQ ID NO: 1. In one embodiment, the targeted sequence bound by a described TALEN is the sequence of SEQ ID NO: 1. Alternatively, the targeted sequence bound by a described TALEN may include a sequence that is antisense, or complementary, to the sequence of SEQ ID NO: 1. In one embodiment, the targeted sequence bound by a described TALEN is a sequence that is antisense, or complementary, to the sequence of SEQ ID NO: 1. In another embodiment the targeted sequence bound by a described TALEN includes the sequence of SEQ ID NO: 3. In one embodiment, the targeted sequence bound by a described TALEN is the sequence of SEQ ID NO: 3. Alternatively, the targeted sequence bound by a described TALEN may include a sequence that is antisense, or complementary, to the sequence of SEQ ID NO: 3. In one embodiment, the targeted sequence bound by a described TALEN is a sequence that is antisense, or complementary, to the sequence of SEQ ID NO: 3.

For the methods disclosed herein, the recombinant DNA-binding polypeptide may also be combined with a polypeptide having nuclease activity, such as a zinc-finger domain or a transcription activator-like effector (TALE) domain fused to a nuclease protein, or a fragment thereof. In some embodiments the polypeptide having nuclease activity that is fused with the recombinant DNA-binding polypeptide is the fokI nuclease, or a derivative or fragment thereof that retains the nuclease activity. In the case of a recombinant DNA-binding polypeptide produced from a TALE domain, fusion with a polypeptide having nuclease activity forms a transcription activator-like effector nuclease (TALEN).

Some of the TALEN embodiments of use in the disclosed methods are designed to specifically target a genomic sequence that falls within the sequence of SEQ ID NO: 19, or its corresponding antisense sequence, such as, for example, the sequence of SEQ ID NO: 1 or 3. In one embodiment the TALE domain includes the amino acid sequence of SEQ ID NO: 7. In another embodiment the TALE domain includes an amino acid sequence of SEQ ID NO: 10. In further embodiments a TALE domain is fused to a polypeptide having nuclease activity to form a TALEN. One TALEN of use in the methods disclosed herein is a TALE domain that includes the amino acid sequence of SEQ ID NO: 7 incorporated into a polypeptide having nuclease activity. In one such embodiment, the amino acid sequence of SEQ ID NO: 7 is incorporated into a polypeptide that also includes a fokI nuclease, or a fragment thereof. For example, the amino acid sequence of SEQ ID NO: 7 may be incorporated into a polypeptide that also includes the amino acid sequence of SEQ ID NO: 13. One embodiment of a polypeptide where the amino acid sequence of SEQ ID NO: 7 is incorporated with the amino acid sequence of SEQ ID NO: 13, is the polypeptide of SEQ ID NO: 8. One TALEN of use in the methods disclosed herein is a TALE domain that includes the amino acid sequence of SEQ ID NO: 10 incorporated into a polypeptide having nuclease activity. In one such embodiment, the amino acid sequence of SEQ ID NO: 10 is incorporated into a polypeptide that also includes a fokI nuclease, or a fragment thereof that retains nuclease activity. For example, the amino acid sequence of SEQ ID NO: 10 may be incorporated into a polypeptide that also includes the amino acid sequence of SEQ ID NO: 13. One embodiment of a polypeptide where the amino acid sequence of SEQ ID NO: 10 is incorporated with the amino acid sequence of SEQ ID NO: 13, is the polypeptide of SEQ ID NO: 11.

The TALE constructs of use in the methods disclosed herein can be used to target specific DNA sequences, such as a genomic sequence of interest in an MSC. When coupled with a polypeptide having nuclease activity to form a TALEN, these constructs can be used to target a specific polynucleotide of interest for modification in the genome of the MSC. In one embodiment the described TALE domain includes the amino acid sequence of SEQ ID NO: 7 which can target the sequence of SEQ ID NO: 1 specifically. In another embodiment the TALE domain includes an amino acid sequence of SEQ ID NO: 10 which can target the sequence of SEQ ID NO: 3 specifically. In further embodiments a described TALE domain is fused to a polypeptide having nuclease activity to form a TALEN. One TALEN described herein is a TALE domain that includes the amino acid sequence of SEQ ID NO: 7 incorporated into a polypeptide having nuclease activity, which can target the sequence of SEQ ID NO: 1 specifically. In one such embodiment, the amino acid sequence of SEQ ID NO: 7 is incorporated into a polypeptide that also includes a fokI nuclease, or a fragment thereof that retains nuclease activity, and can target the sequence of SEQ ID NO: 1 specifically and mediate cleavage of a DNA sequence proximal to the segment where the polynucleotide is bound. For example, the amino acid sequence of SEQ ID NO: 7 may be incorporated into a polypeptide that also includes the amino acid sequence of SEQ ID NO: 13, for specific targeting of the sequence of SEQ ID NO: 1 and cleavage of the polynucleotide sequence proximal to the binding locus. One embodiment of a polypeptide where the amino acid sequence of SEQ ID NO: 7 is incorporated with the amino acid sequence of SEQ ID NO: 13, is the polypeptide of SEQ ID NO: 8, which can specifically bind the sequence of SEQ ID NO: 1 and cleave the polynucleotide sequence proximal to the binding locus.

Another TALEN of use in the methods disclosed herein is a TALE domain that includes the amino acid sequence of SEQ ID NO: 10 incorporated into a polypeptide having nuclease activity, which can target the sequence of SEQ ID NO: 3 specifically. In one such embodiment, the amino acid sequence of SEQ ID NO: 10 is incorporated into a polypeptide that also includes a fokI nuclease, or a fragment thereof that retains nuclease activity, and can target the sequence of SEQ ID NO: 3 specifically and mediate cleavage of a DNA sequence proximal to the segment where the polynucleotide is bound. For example, the amino acid sequence of SEQ ID NO: 10 may be incorporated into a polypeptide that also includes the amino acid sequence of SEQ ID NO: 13, for specific targeting of the sequence of SEQ ID NO: 3 and cleavage of the polynucleotide sequence proximal to the binding locus. One embodiment of a polypeptide where the amino acid sequence of SEQ ID NO: 10 is incorporated with the amino acid sequence of SEQ ID NO: 13, is the polypeptide of SEQ ID NO: 11, which can specifically bind the sequence of SEQ ID NO: 3 and cleave the polynucleotide sequence proximal to the binding locus.

Modifications can be made to the described subject matter resulting in substantially similar polypeptides and constructs that carry out essentially the same functions, in substantially the same way, as the described polynucleotide-binding polypeptides and related nuclease constructs. For example, zinc-finger-based constructs, or CRISPR technology, can be used to target the loci described herein to modify a genome of a cell or chromosomal DNA. Accordingly, such variations are considered to be within the scope of the present disclosure.

Polynucleotides and vectors are also of use in the methods disclosed herein. The polynucleotides encode the polypeptides disclosed above. In some embodiments, the polynucleotides and vectors encode recombinant DNA-binding polypeptides, zinc-finger or TALE domains, nuclease proteins or polypeptides, fusion proteins produced from the fusion of DNA-binding polypeptides and nuclease proteins or polypeptides, such as TALENs. In some embodiments the expression of the polypeptides encoded by the vectors are controlled by an inducible promoter. Suitable promoters include, but are not limited to, the doubecourtin (DCX) promoter and glial fibrillary acidic protein (GFAP). In other embodiments the expression of the polypeptides encoded by the vectors are controlled by a repressible promoter. Cells of the present invention can be modified by the described vectors, for example transfected cells or cells having an expression product of the vectors.

The polypeptides described herein can be encoded by a variety of polynucleotides due to the degeneracy of the genetic code. Thus, the polynucleotides provided herein may be altered to encode the same corresponding amino acid sequences disclosed herein, as would be understood by those skilled in the art. Accordingly, the use of such varied polynucleotide sequences should be considered within the scope of the presently claimed methods. The amino acid sequence of SEQ ID NO: 7 may be encoded by a nucleotide having the sequence of SEQ ID NO: 2. The amino acid sequence of SEQ ID NO: 8 may be encoded by a nucleotide having the sequence of SEQ ID NO: 5. The amino acid sequence of SEQ ID NO: 10 may be encoded by a nucleotide having the sequence of SEQ ID NO: 4. The amino acid sequence of SEQ ID NO: 11 may be encoded by a nucleotide having the sequence of SEQ ID NO: 6. The amino acid sequence of SEQ ID NO: 13 may be encoded by a nucleotide having the sequence of SEQ ID NO: 14.

Furthermore, the vectors of use in the methods disclosed herein, that express the polynucleotides, or produce the polypeptides, may be substituted for other vectors having similar functional capabilities that would be understood by those skilled in the art having benefit of the present disclosure. In one embodiment, the polypeptide of SEQ ID NO: 8 may be produced by the polynucleotide of SEQ ID NO: 9. In another embodiment the polypeptide of SEQ ID NO: 11 may be encoded by the polynucleotide of SEQ ID NO: 12.

Provided herein are donor polynucleotides that may be inserted into the genome of the cell. In some embodiments the donor polynucleotides are double-stranded polynucleotides with sense and/or antisense strand polynucleotide overhangs that are at least partially complementary to corresponding polynucleotide overhangs of cleaved genomic DNA to facilitate insertion of the donor polynucleotide with the cleaved genomic DNA. In additional embodiments the donor polynucleotides are single-stranded polynucleotides with sense and/or antisense strand polynucleotide overhangs (portions) that are at least partially complementary to corresponding polynucleotide overhangs of cleaved genomic DNA to facilitate insertion of the donor polynucleotide with the cleaved genomic DNA. In some embodiments the donor polynucleotide may express a polypeptide once inserted into the genome of the cell or a cell differentiated therefrom. In some embodiments the expressed polypeptide can be a protein that can function to induce cell differentiation or maturation to proceed in a particular manner, such as toward a specific cell lineage. In some embodiments the expression of a polypeptide by the donor polynucleotide may be controlled by an inducible promoter, such as a promoter expressed in differentiated cells. In other embodiments, the expression of a polypeptide by the donor polynucleotide may be controlled by a repressible promoter. In still other embodiments the donor polynucleotide may encode more than one polypeptide, for example, the donor polynucleotide may include an expression cassette having a plurality of genes. In certain embodiments where the donor polynucleotide encodes more than one polypeptide, the donor polynucleotide may have inducible promoters to regulate the expression of certain genes and repressible promoters to regulate the expression of other genes.

As shown herein, these sites can be targeted in multiple iPSC lines to generate reporter systems while retaining pluripotent characteristics. These sites have previously been shown not to be silenced (Luo et al. Stem cells translational medicine 2014 3:821-835; Macarthur et al. Stem cells and development 2012 21:191-205). Different promoters were evaluated and the CMV early enhancer/chicken beta actin (CAG) promoter appeared the most stable and was used for subsequent experiments. Additionally, two different reporters were evaluated: Nanoluc® (luciferase) for quantitation and sensitivity, and copGFP for its fluorescence intensity and stability. Both reporters worked efficiently and a subset of the data is shown in FIG. 1.

The constructs and the schemas of generating knock in (KI) iPSC lines at the two safe harbor sites with the exemplary reporter copGFP driven by the constitutively active CAG promoter are illustrated in FIG. 1A-B. A well-characterized integration-free iPSC line, XCL1, was used as the parental line for all gene-targeting work described herein unless specified otherwise. The Chr 19 site was first targeted and 37 colonies were analyzed for AAVS1-copGFP line by PCR after drug selection and single cell colony cloning. Of these colonies, 12 clones were targeted on one allele and 25 were targeted to both alleles. Similar targeting efficacy was observed for the Chr 13 site. A representative example of a monoallelic (heterozygote) and biallelic (homozygote) is shown in FIG. 1C-D (homozygotes for the AAVS1-copGFP line and heterozygotes for the Chr13-copGFP line). Further sequencing of the PCR products confirmed the successful integration of donor constructs into appropriate genome loci (FIGS. 1C and 1D).

The reporter lines engineered by each of the safe harbor integration strategies were then validated. Genomic stability of a representative line, the AAVS1-copGFP line was determined. When directly differentiated toward the neural lineage, the copGFP reporter in this RI line was not silenced as evidenced by continuous expression of GFP in nestin-positive neural stem cell (NSC) (FIG. 1E). No gene silencing was observed during random differentiation via embryoid body formation as cells of the three germ layers differentiated from the AAVS1-copGFP line remained GFP-positive.

To confirm that this safe harbor KI approach can be generalized, similar reporters were created in another well-characterized integration-free line, XCL5 (NCRM5). As an example, a Chr13-Nanoluc®-HaloTag® line was generated, similar to the Chr13-copGFP line in which a Nanoluc®/HaloTag® reporter was used instead of copGFP. This line was differentiated to a pure population of neurons or astrocytes via directed differentiation. Further, no gene silencing in these lineages was confirmed. Taken together, these experiments demonstrate targeting at the safe harbor loci to be both reliable and efficient. The cell lines obtained were stable, karyotypically normal and the reporters did not silence on random or directed differentiations. In addition, both sites could be targeted simultaneously, and both mono-allelic and biallelic subclones could be identified.

Figure 2A:
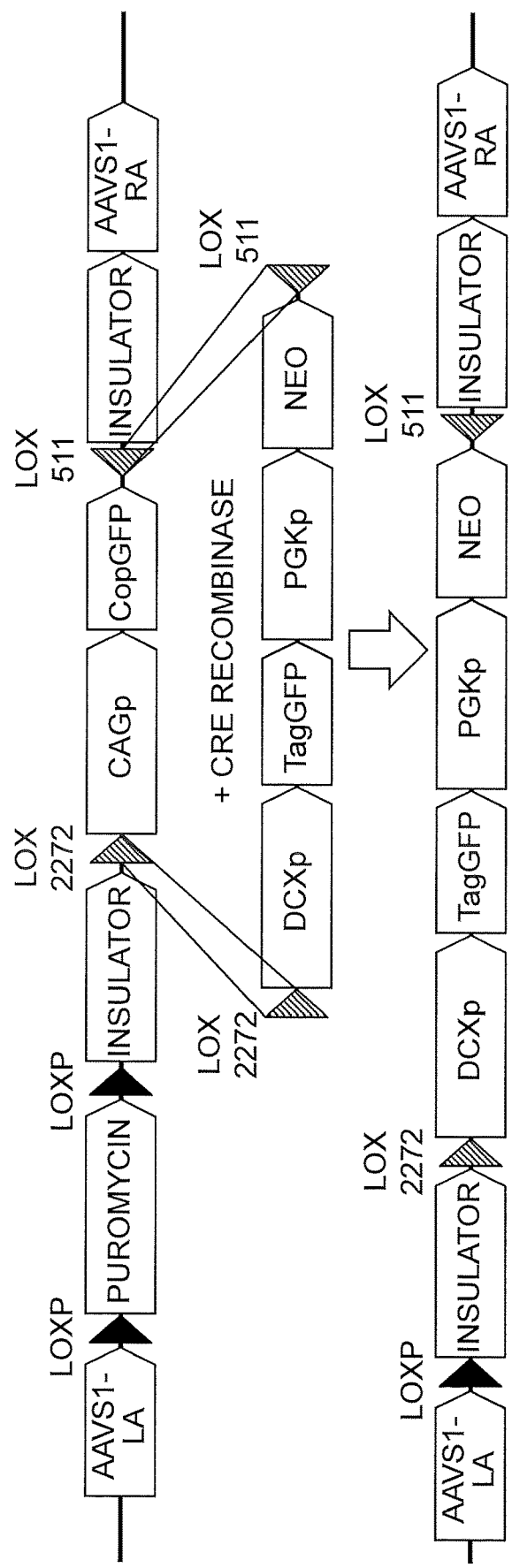

Rapid Exchanging of Reporter Cassettes in Safe Harbors in iPSC and Progenitor Cells Using a Master Cell Line Strategy While ZFN and TALEN increased targeting efficiency several-fold compared to the traditional gene targeting methods, their efficiency may not be high enough to target non-pluripotent cells. This may be important when the differentiation process is very long or genes have toxic effects at some stages. Accordingly, in the present invention, the safe harbor site targeting strategy was modified by utilizing constructs with multiple Lox sites, which allowed for easy replacement of one reporter or promoter with another by Cre-recombinase mediated cassette exchange (RMCE). An nonlimiting example of such a vector design is illustrated in FIG. 2A. In this construct, the CAG promoter driving the copGFP reporter cassette was inserted between lox2272 and lox511 sites with the appropriate orientation for RMCE. In addition, a puromycin resistant gene flanked by two different loxP sites was inserted at the endogenous promoter of AAVS1. Two insulator sites were also added in this line to prevent copGFP silencing. To generate new reporter lines, daughter constructs containing any gene-specific or ubiquitous promoter driving a reporter gene can be inserted between a lox2272 and a lox511 site, and drug selection and loss of the previous insert can be used to identify appropriate clones.

Figure 2C:
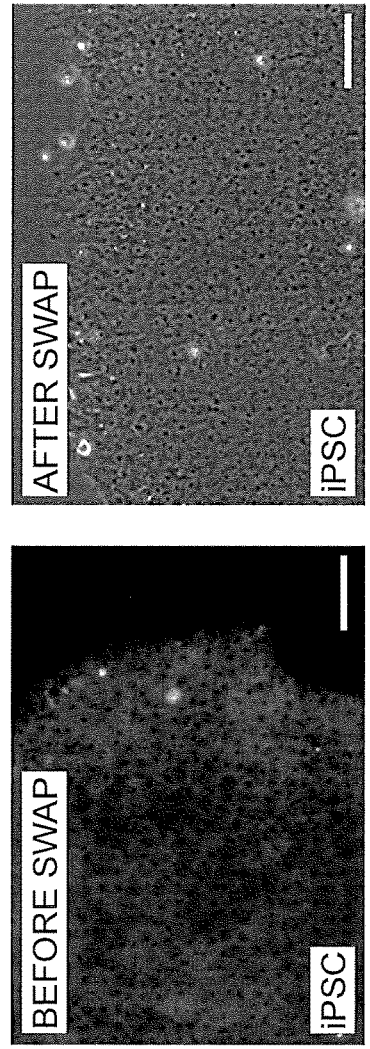
Figure 2B:
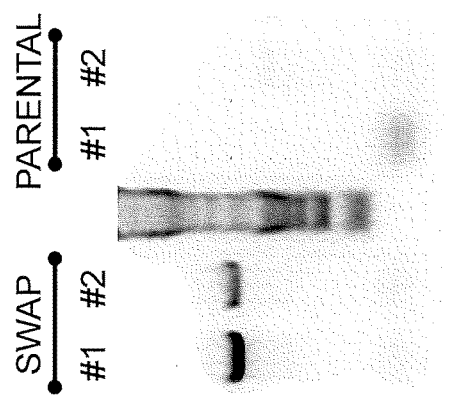

This strategy was tested by replacing GFP driven by the ubiquitous CAG promoter in the AAVS1-copGFP line with a promoter-reporter construct using the neuronal lineage-specific promoter doublecortin (DCX) driving TagGFP (see FIG. 2) or Nanoluc®. In the DCX daughter construct, DCXp-TagGFP, a DCX promoter driving TagGFP together with a PGK promoter driving Neomycin resistant gene was cloned between lox2272 and lox511 sites (see FIG. 2A). In order to induce the RMCE, DCXp-TagGFP construct was co-transfected with a plasmid expressing Cre recombinase by the PGK promoter, into an established AAVS1-copGFP (a homozygote clone) iPSC line. After ROME, colonies that had lost green fluorescence were identified and picked for PCR verifications. Using primers designed specifically for targeting the "parental" and "swap" sequences, iPSC clones were identified where cassette exchange had been successful (see FIG. 2B). Before cassette exchange, the master iPSC line AAVS1-copGFP constitutively expresses green fluorescence and is puromycin resistant. In the presence of Cre recombinase and DCX daughter construct, the puromycin gene was deleted via Cre-loxP mediated recombination, and "CAGp-copGFP" was replaced by the "DCXp-TagGFP-PGKp-Neo" cassette. Thus, the new reporter line, referred to herein as DCXp-TagGFP, is not puromycin but neomycin resistant and is not fluorescent at the iPSC stage (see FIG. 2C).

To confirm functionally appropriate expression in the DCXp-TagGFP reporter line created by cassette exchange, a directed differentiation protocol was used to induce neuronal differentiation in accordance with procedures described by Yan et al. (Stem cells translational medicine 2013 2:862-870). As the cells differentiated toward the neuronal lineage, GFP-positive cells appeared (see FIG. 2D). ICC staining 6 days after differentiation confirmed that all green cells were specifically located with DCX antibody positive neurons (see FIG. 2D), validating the specificity of the DCXp-TagGFP reporter line.

To further confirm the utility of the master iPSC line strategy, it was determined whether the RMCE can be extended to intermediate/progenitor stage cells as well. For these experiments, NSC were derived from the AAVS1-copGFP iPSC line, which maintained strong green fluorescence through differentiation (see FIGS. 1E and 2E). Following the same RMCE procedures as described for the iPSC (see FIG. 2A), DCXp-TagGFP daughter construct and Cre-expressing plasmid were co-transfected into AAVS1-copGFP NSC. No drug selection was used to enrich cells with successful RMCE, since the goal for this experiment was not to isolate single clones of NSC with correct cassette exchange. Instead, the entire cell population was analyzed and cells losing green fluorescence post transfection were identified by fluorescence microscopy, indicating the successful event of RMCE (see FIG. 2E). Junction PCR was used to confirm that cassette exchange was indeed correctly induced in a subset of the NSC (see FIG. 2F). Overall these results showed that isogenic subclones can be rapidly generated at multiple stages of differentiation, which should allow expression of deleterious genes at specific stages of development.

Generation and Lineage-Specific Expression of KI Reporters

Figures 3A, 3B:
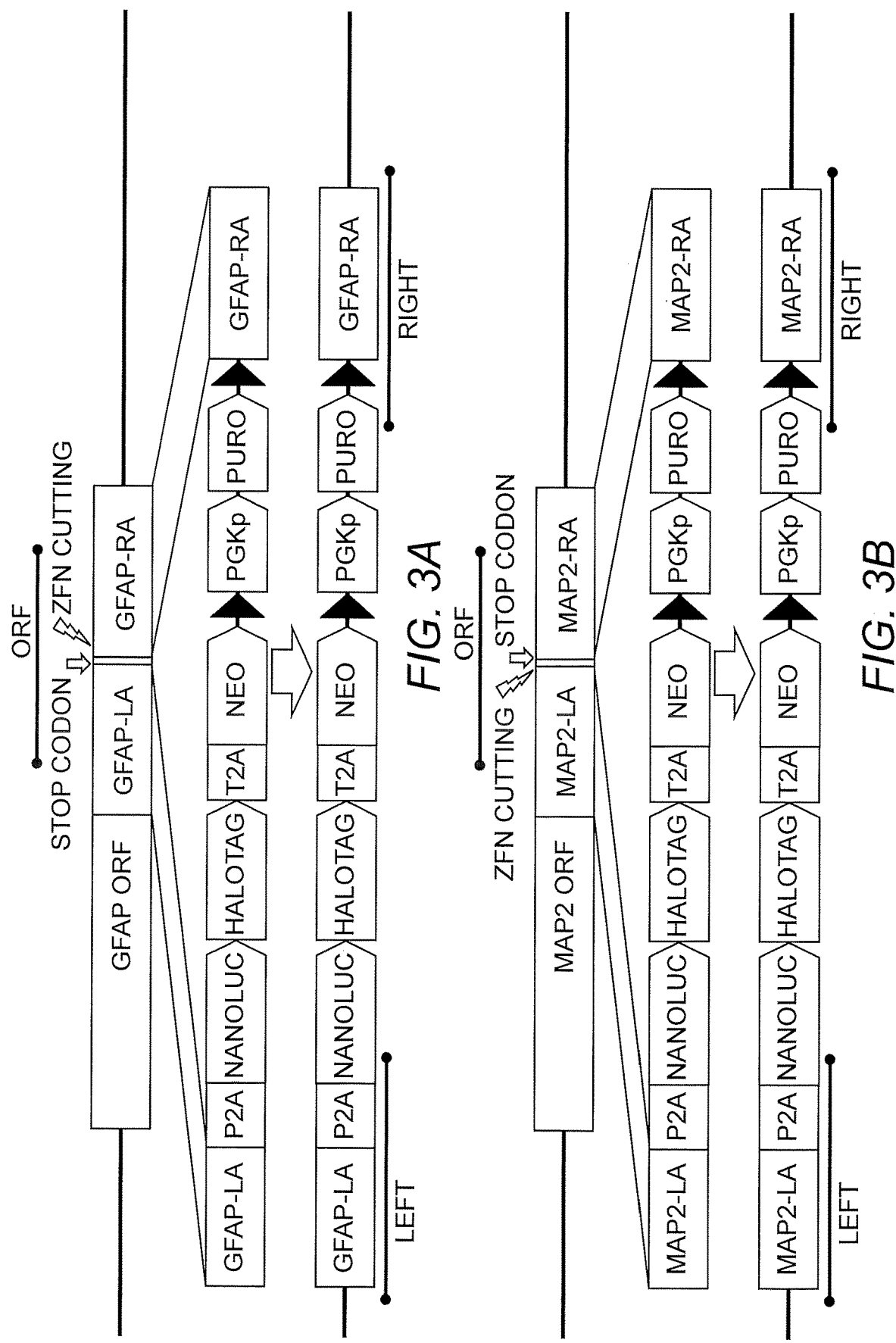
FIGS. 3A through 3D. Generation of knock-in lines at lineage specific genes.
Figures 3C, 3D:
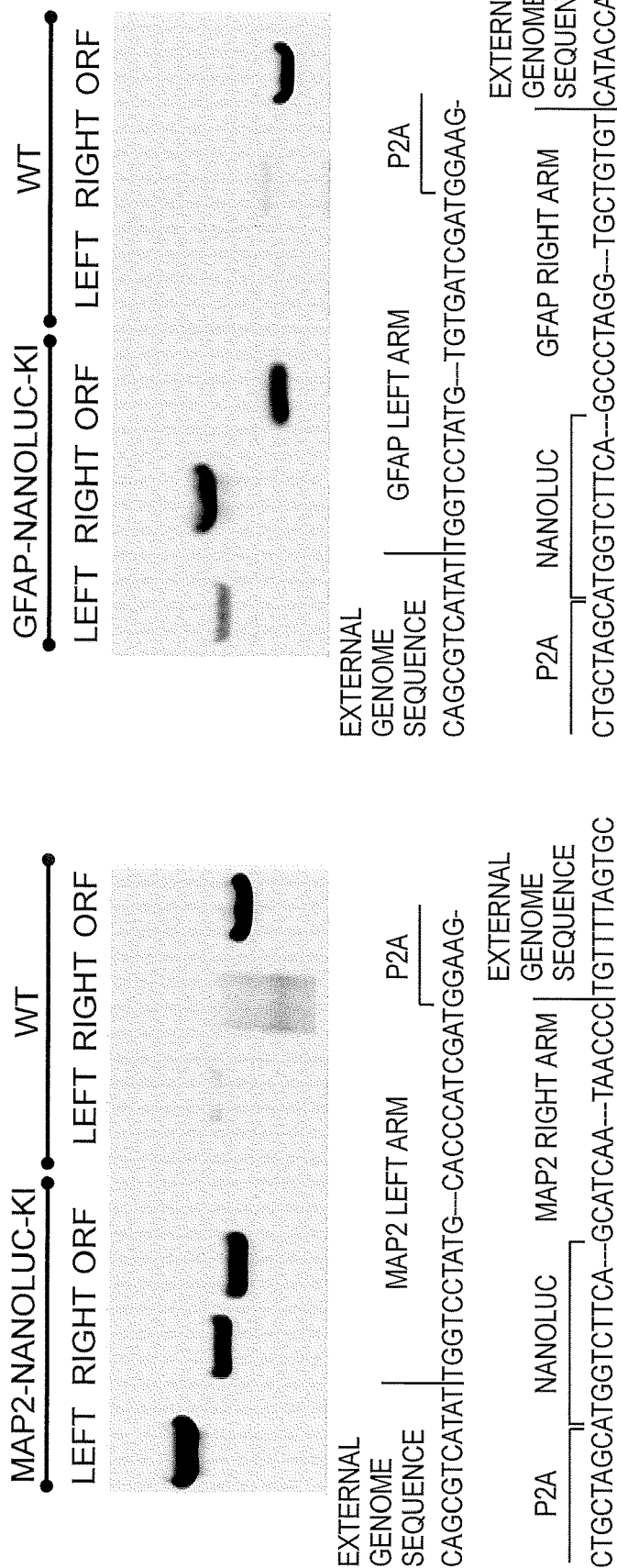

Although lineage-specific constructs for some genes are available and some fragments are sufficiently small that they could be targeted to the safe harbor loci (see above DCX-copGFP reporter), a KI strategy in genes that are expressed in specific lineages is desirable as it allows for the development of assays to identify regulators of development. A Nanoluc®-HaloTag® construct (see FIG. 3) was selected to knock into the endogenous MAP2 locus, and the same reporter construct in endogenous GFAP allele. Monallelic lines were produced and the 3' prime end of the gene was targeted to allow expression of normal levels of the endogenous gene. Both KI reporter lines were made in the XCL1 iPSC line to show that isogenic subclones could be obtained. Further, the same construct has been used in other NCRM lines. Specifically, ZFN pairs targeting the C-term of GFAP or MAP2 genes were designed and optimized. One pair cutting at ~130 bp after the stop codon of GFAP ORF and ZFNs targeting ~90 bp before the stop codon of MAP2 gene were selected for these experiments (FIGS. 3A and 3B). A donor vector consisting of a reporter cassette of a P2A peptide, a Nanoluc® luciferase gene fused with a HaloTag®, followed by a neomycin resistance gene was designed to be in frame with the C-terminal of the targeted genes (see FIGS. 3A and 33). After co-transfection with the donor vector and mRNA of the respective ZFN pair, and appropriate drug selection, 35 colonies from each line were picked for further analysis. Successful insertion of the reporter genes to either GFAP or MAP2 gene was confirmed by both PCR and sequencing analyses for 33 GFAP and 4 MAP2 clones (see FIGS. 3C and 3D). Four clones of each reporter line were selected and verified to be heterozygotes (see FIGS. 3C and 3D). One of each validated GFAP-Nanoluc®-KI and MAP2-Nanoluc®-KI clone was chosen for further analysis as described below.

Figure 4E:
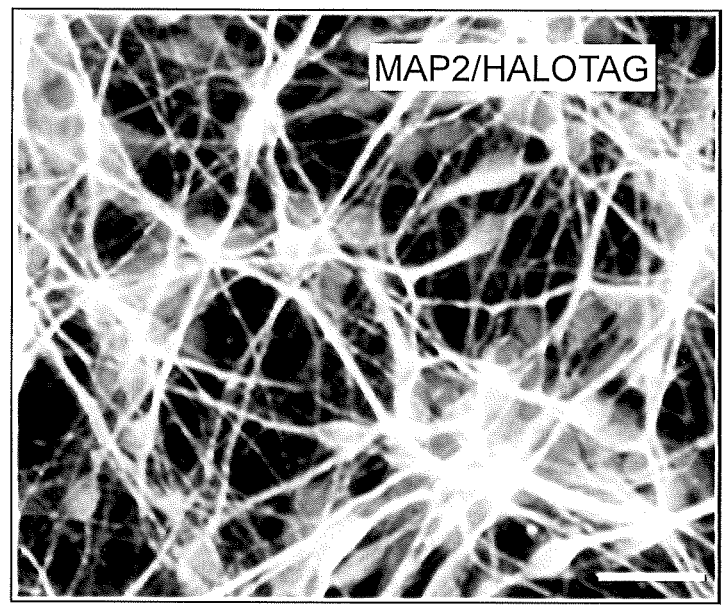
Figure 4D:
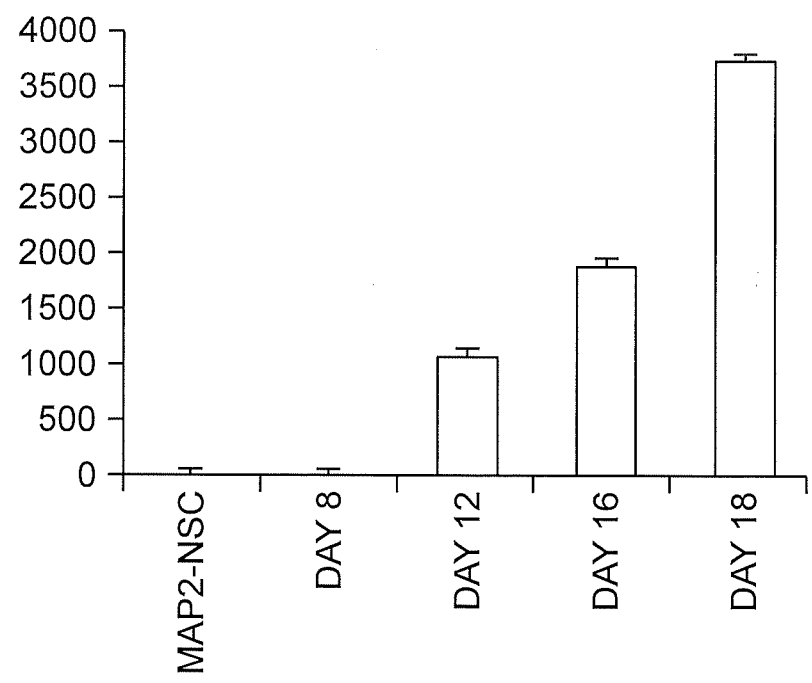
Figure 5:
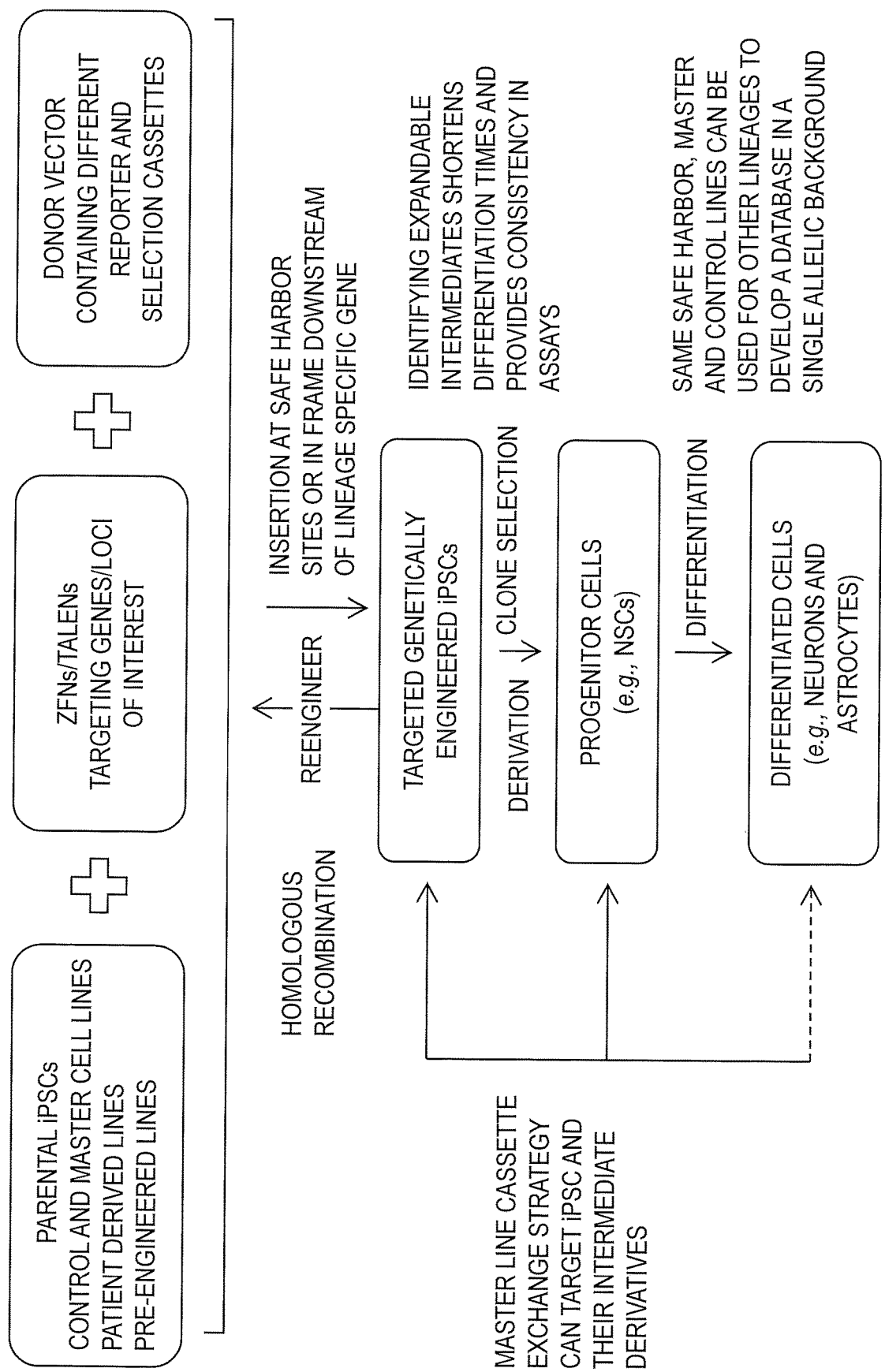
FIG. 5. Summary of different approaches to generate reporter lines in safe harbors and in endogenous lineage-specific genes. Genetic modification techniques (ZFNs or TALEN) were used in combination with carefully designed donor vectors to target and modify genes/loci-of-interest in selected parental iPSC lines. The parental iPSC can be well-established control lines, patient-derived lines, pre-engineered lines or master lines for the quick swapping strategy. Depending on the donor vectors and targeting genes/loci, parental iPSC can be engineered or re-engineered into different lines expressing either constitutively active reporter genes at the safe harbors or reporter genes that are in frame downstream of lineage-specific genes. These targeted genetically engineered iPSC can be derived into progenitor cells and further differentiated into different cell types for numerous screening purposes. Additionally, a master line cassette exchange strategy was developed providing the opportunity to quickly and efficiently generate different reporter lines at the safe harbor sites. Using this strategy, successful targeting to both iPSC and the progenitor cells (solid arrows) was demonstrated. It is expected that this strategy can also be applied directly to the differentiated cells (dotted arrow).

The positive expression of pluripotency markers and a normal karyotype in prolonged culture of both GFAP-Nanoluc®-KI and MAP2-Nanoluc®-KI iPSC lines were first confirmed. Next neural differentiation was induced via NSC formation from these two iPSC lines and the expression of the reporter genes, Nanoluc® and HaloTag®, was tracked during lineage-specific differentiation (see FIG. 4). No luciferase signal was detected in GFAP-Nanoluc®-KI or MAP2-Nanoluc®-KI lines or NSC derived from them (see FIGS. 4A, 4C, 4D and 4F).

For GFAP-Nanoluc®-KI NSC, the expression of luciferase and HaloTag® during astrocyte differentiation was monitored using a well-established protocol (Shaltouki et al. Stem cells 2013 31:941-952). Starting from day 18 after the NSC stage, the luminescence intensity increased gradually as the cells differentiated to astrocytes (see FIG. 4A). In order to visualize expression of the reporter gene during differentiation, ligand that covalently binds, to HaloTag® was used to label live GFAP-Nanoluc®-KI cells at different time points during astrocyte differentiation. HaloTag®-labeled fluorescent cells were only observed after the differentiation, further confirming that the reporters were turned on specifically by the GFAP promoter as the cells differentiated into astrocytes (see FIG. 4C). The differentiated GFAP-Nanoluc®-KI cells (D23 post differentiation) were then tested by immunostaining and co-localization of GFAP and HaloTag® antibodies was found in nearly 100% of the cells, indicating that the reporter genes in GFAP-Nanoluc®-KI only turned on in the GFAP-positive cells (see FIG. 4B).

Using a similar strategy, the expression of Nanoluc® and HaloTag® reporter genes was monitored in the MAP2-Nanoluc®-KI cells during neuronal differentiation. A 2-week differentiation protocol was used to generate a pure population of mixed neurons from the NSC (Swistowska et al. Stem cells and development 2010 19:71-82). No detectable luminescence was observed until 12 days post differentiation (see FIG. 4D). No fluorescence was detected from HaloTag® expression in MAP2 NSC prior to differentiation (see FIG. 4F). Expression of HaloTag® was observed as more and more cells differentiated into neurons (see FIG. 4E). Importantly, HaloTag® antibody only stained the MAP2-positive neurons, indicating the specific expression of the reporter from the endogenous MAP2 promoter. These results signify that a single luciferase or HaloTag® gene is sufficiently sensitive to allow for live tracking of differentiation events.

To determine the minimal numbers of cells required for detectable level of Nanoluc®, the luminescence level of both GFAP-Nanoluc®-KI astrocytes and MAP2-Nanoluc®-KI neurons was measured at different cell densities (see FIG. 4G). Less than $1\times10^4$ cells were required for either GFAP-Nanoluc®-KI astrocytes or MAP2-Nanoluc®-KI neurons to be detected by luminescence in a 96-well format. This result suggested that the GFAP-Nanoluc®-KI and MAP2-Nanoluc®-KI reporters can be used to effectively and accurately track astrocytes or neurons during differentiation with small numbers of cells and in a high-throughput manner.

To further demonstrate that clones with multiple reporters can be made rapidly, a stock of NSC was generated from the MAP2-Nanoluc®-KI subclone targeting the safe harbor locus at the NSC stage. The targeted clone (the MAP2-Nanoluc®-KI line) could be re-targeted and a dual reporter line could be readily generated. Even higher efficiency was obtained when the clone was targeted at the iPSC stage, which was comparable to those seen in an untargeted line.

Thus, as shown herein, by combining safe harbor gene editing, cassette exchange tools, and the identification of lineage specific gene loci, the present invention provides a useful means for rapidly developing single and multiplexed reporters that provide investigators the ability to develop a repertoire of assays using reporters appropriate for their particular need. Further, the Nanoluc®-HaloTag® reporter construct disclosed herein offers several advantages. For example, it allows for simultaneous quantitative assessment and fluorescent imaging on demand for time-lapse imaging. By using small molecule ligands to HaloTag®, one also has the advantage of choosing fluorescent signals, as its labeling is transient, which allows for other imaging modalities to be used when necessary. In addition, antibodies to the HaloTag® are available allowing antibody labeling in fixed cells for archival purposes.

Further, the limited availability of human cells of the central nervous system make iPSC derived neural derivatives a promising cell source for drug discovery and for improvement of existing drug development workflow, specifically for the evaluation of toxicity and efficacy of lead compounds. Most neural differentiation protocols currently available, however, produce a heterogeneous population of neuron and glial cells, making it difficult to interpret the mechanism of action of a given compound. Using the neural lineage-specific KI reporter approach of the present invention mitigates this problem through use of a donor vector containing dual reporters of luciferase and HaloTag® attached to the C-terminal of an endogenous lineage-specific gene. For example, using this approach, the MAP2 gene was targeted for neuron-specific reporter and the GFAP gene was targeted for astrocyte-specific reporter. Lineage-specific expression of the reporters was then validated during lineage-specific differentiation. This MAP2-Nanoluc®-KI line allows for real-time monitoring of neuronal differentiation, and the luciferase activity in the culture reflects the percentage of neurons. The non-disruptive assay format enables accurate and quantitative measurement of any compound on neurons specifically. Likewise, the GFAP-Nanoluc®-KI line allows for tracking and quantitative measurement of astrocytes in culture. The fact that as few as $10^4$ cells (neurons or astrocytes) from these KI lines were needed to detect the luciferase activity in culture media makes these reporters/assays applicable for high-throughput and high content screening.

Further, because drug selection is incorporated via a T2A site downstream of the lineage specific promoter in the present invention, it is possible to purify neurons and astrocytes for assays. Likewise, cells can be sorted using the fluorescent label allowing one to combine screening with gene expression analysis.

In addition, cassette exchange in iPSC and NSCs in accordance with the present invention showed that clones can be rapidly generated in multiple stages of development. While experiments described in detail herein were performed in the neuronal lineage, the platform of the present invention has also been demonstrated to work in mesenchymal stem cells and astrocyte precursors and is expected to work with any other intermediate progenitor as well. The ability to use multiple reporters in the same site for different purposes is an invaluable benefit to having to generate new reporters or new lines and test their specificity and quality each time.

An additional advantage of the present invention is that the same safe harbors, master and control lines can be used for other lineages. This will allow for development of a database of drug responses and effects of a mutation in a single pathway in multiple cell types from a single allelic background.

The following nonlimiting examples are provided to further illustrate the present invention.

EXAMPLES

Example 1: iPSC Culture and Gene Targeting by ZFN/TALENs

A subclone of each NCRM1 and NCRM5 integration-free iPSC line (NIH CRM), named XCL1 and XCL5, was obtained from XCell Science (Novato, CA) and used as the parental cells for all engineered work described in these examples. iPSC were cultured as in accordance with procedures described by Lie et al. (Methods in molecular biology 2012 873: 237-246) and Zou et al. Blood 2011 117:5561-5572) and maintained in feeder-free conditions on Matrigel (BD Biosciences, CA) coated dishes using mTeSR™1 media (STEMCELL Technologies Inc., Vancouver, Canada) following the manufacturer's protocols. TALEN expression plasmids targeting safe harbor sites in Chr.13 and Chr.19 (AAVS1) were provided by NIH and comprise sequences set forth herein in the Section entitled Sequence Listing. ZFN expression plasmids targeting the C-term of MAP2 and GFAP genes were purchased from Sigma (St. Louis, MO). Each plasmid DNA was linearized by XbaI for mRNA production and purification following modified manufacturer's protocols.

Example 2: Donor Vector Design and Construction

A backbone vector containing a puromycin resistant gene flanked by two loxP sites and a CAG promoter driving copGFP cassette was constructed between the lox2272 and lox511 sites. Insulator expressing genes were used to generate AAVS1-copGFP donor vector targeting to the AAVS1 site at Chr.19 (see FIG. 1A). A 754 bp left homologous arm and an 838 bp right homologous arm were amplified by PCR from XCL1 (Xcell Inc, CA) gDNA and cloned into the backbone vector. For Chr13-copGFP, a similar backbone vector was used (the puromycin resistant gene was replaced by a PGK promoter driven neomycin resistant gene) and inserted with a 832 bp left homologous arm and a 796 bp right homologous arm amplified from the Chr13 safe harbor region where designed TALENs are targeting to.

Another backbone vector containing a P2A peptide, Nanoluc® reporter gene fused with a downstream HaloTag®, a T2A peptide in frame with a Neomycin resistant gene and a puromycin resistant gene flanked by two loxP sites was designed and constructed for targeting different genes to generate lineage-specific reporter donor vectors. A 1069 bp left homologous arm right before the stop codon of MAP2 gene was PCRed from XCL1, and then cloned into the backbone vector upstream and in frame with the P2A peptide. A 1084 bp fragment was cloned in as right homologous arm to generate the MAP2-Nanoluc®-KI donor vector. For the GFAP-Nanoluc®-KI donor vector, a 1022 bp fragment right before the stop codon and a 1020 bp fragment after the stop codon was cloned into backbone vector as the left and right homologous arm, respectively.

Example 3: Reporter iPSC Lines Generation

Prior to nucleofection, XCL1 iPS cells were maintained and passed using Accutase (Life Tech., NJ) to make sure cells are growing in monolayer. On the day of nucleofection, single cell suspension cells were generated using Accutase followed by inactivation and washes with HBSS. 4-6 ug of each pair of TALENs/ZFNs RNA was used for nucleofection using Amaxa Human Stem Cell Nucleofection Kit (Lonza, NJ). After nucleofection, cells were plated in mTeSR™1 medium with 10 uM Rock inhibitor. After 2-5 days recovery, cells were treated with appropriate antibiotics. Specifically, 2.5 µg/ml Puromycin (Life Tech., NJ) for AAVS1-copGFP, MAP2-Nanoluc®-KI and GFAP-Nanoluc®-KI lines and 500 µg/ml Neomycin (Life Tech., NJ) for Chr13-copGFP line. Drug resistant colonies were re-plated at low density for single cell cloning. Colonies growing from single cells were screened by PCRs and sequencing to identify targets with correct donor vector integrations. The verified targets were expanded, stored and characterized for future experiments.

Example 4: NSC Derivation and Neural Differentiation

Generation of NSC was accomplished in accordance with procedures described by Swistowski et al. (PLoS one 2009 4:e6233). More specifically, NSC were derived from iPSC lines and were cultured on Matrigel coated dishes in Neurobasal® medium supplemented with 1% nonessential amino acids, 1% GlutaMAX, 1×B-27®, and 10 ng/ml bFGF, and passaged using Accutase. Neuronal differentiation was achieved by culturing NSC in Neuronal Primer media (Xcell inc, CA) on a surface coated with Poly-L-ornithine (2 µg/ml, Sigma, St. Louis, MO) and laminin (10 µg/ml, Life Tech., NJ) at a density of 40-50 k/cm2 for 5-6 days until cells become confluent. Then cells were split with Accutase and were plated onto new poly-ornithine/laminin coated dishes at 40-50 k/cm2 in Neuronal Medium (Xcell inc, CA) to continue differentiation for as long as desired. Astrocyte differentiation from NSC was also carried out on culture dishes or glass cover slips coated with Poly-L-ornithine/laminin in Astrocyte Primer medium (Xcell Inc, CA). Medium was changed every other day and cells have to be split at least 3 times before day 15. On day 18, change media to Astrocyte medium (Xcell inc, CA) and continue differentiation for up to day 35.

Example 5: Cre Recombinase-Mediated Cassette Exchange in iPSC and NSC

The iPSC or NSC master lines (AAVS1-copGFP or Chr13-copGFP) were plated on Matrigel-coated 35 mm dishes. When cells reached 70-80% confluency, plasmid expressing Cre recombinase and daughter construct were co-transfected using Lipofectamine 3000 (Life Tech., NJ) following manufacturer's protocols. For iPSC, cells were selected with appropriate antibiotics to enrich the cell populations with successful cassette exchange. Then drug resistant colonies were further screened using a fluorescence microscope to identify colonies that lost green fluorescence, which were picked, expanded and confirmed by PCR and sequencing.

Example 6: Immunocytochemistry

Immunocytochemistry and staining procedures were performed in accordance with procedures described by Zeng et al. (Stem Cells 2003 21:647-653). Specifically, cells were fixed with 4% paraformaldehyde for 20 minutes at room temperature, blocked in blocking buffer (10% goat serum, 1% BSA, 0.1% Triton X-100) for one hour followed by incubation with the primary antibody at 4° C. overnight in 8% goat serum, 1% BSA, 0.1% Triton X-100. Appropriately coupled secondary antibodies, Alexa488 and Alexa594 (Molecular Probes and Jackson ImmunoResearch Lab Inc.) were used for single or double labeling. All secondary antibodies were tested for cross reactivity and non-specific immune-reactivity. The following primary antibodies were used: Nestin (BD Biosciences, CA), GFAP (DakoCytomation Inc, CA), MAP2 (Sigma, St. Louis) and DCX (Santa Cruz Biotechnology, TX). DAPI was used to label the nuclei.

Example 7: Luciferase Activity Measurement and HaloTag® Detection

Determination of Nanoluc® luciferase activity was measured using Nano-Glo® (assay reagent for bioluminescencel Promega Corporation, WI) Assay System following manufacturer's protocol (Promega, WI). Specifically, 50 μl culture media was mixed with 50 μl of Nano-Glo® Assay Reagent in a 96-well plate for an incubation period of 5 min. Then luciferase activity was measured using a Perkin Elmer Fusion-alpha-FP-HT universal microplate analyzer. Detection of HaloTag® was achieved either in live cells using HaloTag® TMR Ligand following manufacturer's protocol (Promega, WI) or in fixed cells using HaloTag® antibodies (Promega, WI).

What is claimed is:

1. A method of generating a new reporter line, said method comprising utilizing a Cre-recombinase induced cassette exchange strategy in a master cell line comprising a first reporter cassette at a safe harbor site on chromosome 13 and a second reporter cassette at a safe harbor site on chromosome 19, wherein said first and second reporter cassettes each comprise a reporter gene driven by a constitutively active promoter and multiple Lox sites to exchange the first or second reporter cassette in the master cell line with a new reporter cassette, thereby generating a new reporter line with the same isogenic background, wherein the master cell line is integrated with the new reporter cassette at a safe harbor site in the cell and wherein the new reporter cassette comprises a reporter gene driven by a constitutively active promoter and multiple Lox sites.

2. The method of claim 1 wherein the promoter driving the reporter gene is inserted between two Lox sites.

3. The method of claim 1 wherein the promoter is inserted between lox2272 and lox511.

4. The method of claim 1 wherein the cell is a progenitor cell.

5. The method of claim 4 wherein the cell is a pluripotent or multipotent stem cell.

6. The method of claim 5 wherein the cell is an induced pluripotent stem cell.

7. The method of claim 4 wherein the cell is a neural stem cell.

8. The method of claim 1 wherein the cell is a differentiated cell.

* * * * *

```
SEQUENCE LISTING

Sequence total quantity: 39
SEQ ID NO: 1            moltype = DNA  length = 17
FEATURE                 Location/Qualifiers
source                  1..17
                        mol_type = genomic DNA
                        organism = Homo sapiens
SEQUENCE: 1
cttacccttc tcccatt                                                  17

SEQ ID NO: 2            moltype = DNA  length = 1692
FEATURE                 Location/Qualifiers
source                  1..1692
                        mol_type = genomic DNA
                        organism = Homo sapiens
SEQUENCE: 2
ctgacccgg accaagtggt ggctatcgcc agccacgatg gcggcaagca agcgctcgaa    60
acggtgcagc ggctgttgcc ggtgctgtgc caggaccatg gcctgacccc ggaccaagtg  120
gtggctatcg ccagcaacgg tggcggcaag caagcgctca aaacggtgca gcggctgttg  180
ccggtgctgt gccaggacca tggcctgacc ccggaccaag tggtggctat cgccagcaac  240
ggtggcggca agcaagcgct cgaaacggtg cagcggctgt tgccggtgct gtgccaggac  300
catggcctga ccccggacca agtggtggct atcgccagca acattggcgg caagcaagcg  360
ctcgaaacgg tgcagcggct gttgccggtg ctgtgccagg accatggcct gactccggac  420
caagtggtgg ctatcgccag ccacgatggc ggcaagcaag cgctcgaaac ggtgcagcgg  480
ctgttgccgg tgctgtgcca ggaccatggc ctgactccgg accaagtggt ggctatcgcc  540
agccacgatg gcggcaagca agcgctcgaa acggtgcagc ggctgttgcc ggtgctgtgc  600
caggaccatg gcctgactcc ggaccaagtg gtggctatcg ccagccacga tggcggcaag  660
caagcgctcg aaacggtgca gcggctgttg ccggtgctgt gccaggacca tggcctgacc  720
ccggaccaag tggtggctat cgccagcaac ggtggcggca agcaagcgct cgaaacggtg  780
cagcggctgt tgccggtgct gtgccaggac catggcctga ccccggacca agtggtggct  840
atcgccagca acggtggcgg caagcaagct cgaaacgg tgcagcggct gttgccggtg  900
ctgtgccagg accatggcct gactccggac caagtggtgg ctatcgccag ccacgatggc  960
ggcaagcaag cgctcgaaac ggtgcagcgg ctgttgccgg tgctgtgcca ggaccatggc 1020
ctgacccgg accaagtggt ggctatcgcc agcaacggtg gcggcaagca agcgctcgaa 1080
acggtgcagc ggctgttgcc ggtgctgtgc caggaccatg gcctgactcc ggaccaagtg 1140
gtggctatcg ccagccacga tggcggcaag caagcgctcg aaacggtgca gcggctgttg 1200
ccggtgctgt gccaggacca tggcctgact ccggaccaag tggtggctat cgccagccac 1260
gatggcggca agcaagcgct cgaaacggtg cagcggctgt gccggtgct gtgccaggac 1320
catggcctga ctccggacca agtggtggct atcgccagcc acgatggcgg caagcaagcg 1380
ctcgaaacgg tgcagcggct gttgccggtg ctgtgccagg accatggcct gacccgga 1440
caagtggtgg ctatcgccag caacattggc ggcaagcaag cgctcgaaac ggtgcagcgg 1500
ctgttgccgg tgctgtgcca ggaccatggc ctgacccgg accaagtggt ggctatcgcc 1560
agcaacggtg gcggcaagca agcgctcgaa acggtgcagc ggctgttgcc ggtgctgtgc 1620
caggaccatg gcctgaccc ggaccaagtg gtggctatcg ccagcaacgg tggcggcaag 1680
caagcgctcg aa                                                    1692

SEQ ID NO: 3            moltype = DNA  length = 16
FEATURE                 Location/Qualifiers
source                  1..16
                        mol_type = genomic DNA
                        organism = Homo sapiens
SEQUENCE: 3
cccaaaatat atttat                                                   16

SEQ ID NO: 4            moltype = DNA  length = 1590
```

| FEATURE | Location/Qualifiers |
|---|---|
| source | 1..1590<br>mol_type = genomic DNA<br>organism = Homo sapiens |

SEQUENCE: 4

```
ctgaccccgg accaagtggt ggctatcgcc agccacgatg gcggcaagca agcgctcgaa   60
acggtgcagc ggctgttgcc ggtgctgtgc caggaccatg gcctgactcc ggaccaagtg  120
gtggctatcg ccagccacga tggcggcaag caagcgctcg aaacggtgca gcggctgttg  180
ccggtgctgt gccaggacca tggcctgact ccggaccaag tggtggctat cgccagccac  240
gatggcggca agcaagcgct cgaaacggtg cagcggctgt tgccggtgct gtgccaggac  300
catggcctga ccccggacca agtggtggct atcgccagca acattggcgg caagcaagcg  360
ctcgaaacgt gcagcggct gttgccggtg ctgtgccagg accatggcct gaccccggac  420
caagtggtgg ctatcgccag caacattggc ggcaagcaag cgctcgaaac ggtgcagcgg  480
ctgttgccgg tgctgtgcca ggaccatggc tgaccccgg accaagtggt ggctatcgcc  540
agcaacattg gcggcaagca agcgctcgaa acggtgcagc ggctgttgcc ggtgctgtgc  600
caggaccatg gcctgacccc ggaccaagtg gtggctatcg ccagcaacat tggcggcaag  660
caagcgctcg aaacggtgca gcggctgttg ccggtgctgt gccaggacca tggcctgacc  720
ccggaccaag tggtggctat cgccagcaac ggtggcggca agcaagcgct cgaaacggtg  780
cagcggctgt tgccggtgct gtgccaggac catggcctga ccccggacca agtggtggct  840
atcgccagca acattggcgg caagcaagcg ctcgaaacgg tgcagcggct gttgccggtg  900
ctgtgccagg accatggcct gaccccggac caagtggtgg ctatcgccag caacggtggc  960
ggcaagcaag cgctcgaaac ggtgcagcgg ctgttgccgg tgctgtgcca ggaccatggc 1020
ctgaccccgg accaagtggt ggctatcgcc agcaacattg gcggcaagca agcgctcgaa 1080
acggtgcagc ggctgttgcc ggtgctgtgc caggaccatg gcctgacccc ggaccaagtg 1140
gtggctatcg ccagcaacgg tggcggcaag caagcgctcg aaacggtgca gcggctgttg 1200
ccggtgctgt gccaggacca tggcctgacc ccggaccaag tggtggctat cgccagcaac 1260
ggtggcggca agcaagcgct cgaaacggtg cagcggctgt tgccggtgct gtgccaggac 1320
catggcctga ccccggacca agtggtggct atcgccagca acgtggcgg caagcaagcg 1380
ctcgaaacgt gcagcggct gttgccggtg ctgtgccagg accatggcct gaccccggac 1440
caagtggtgg ctatcgccag caacattggc ggcaagcaag cgctcgaaac ggtgcagcgg 1500
ctgttgccgg tgctgtgcca ggaccatggc ctgaccccgg accaagtggt ggctatcgcc 1560
agcaacggtg gcggcaagca agcgctcgaa                                  1590
```

| SEQ ID NO: 5 | moltype = DNA  length = 2889 |
|---|---|
| FEATURE | Location/Qualifiers |
| source | 1..2889<br>mol_type = genomic DNA<br>organism = Homo sapiens |

SEQUENCE: 5

```
gtggacttga ggacactcgg ttattcgcaa cagcaacagg agaaaatcaa gcctaaggtc   60
aggagcaccg tcgcgcaaca ccacgaggcg cttgtgggc atggcttcac tcatgcgcat  120
attgtcgcgc tttcacagca ccctgcgcg cttgggacgt ggctgtcaa ataccaagat  180
atgattgcgg ccctgcccga agccacgcac gaggcaattg taggggtcgt taaacagtgg  240
tcggagcgc gagcacttga ggccttgctg actgtggcgg gtgagcttag ggggcctccg  300
ctccagctcg acaccgggca gctgctgaag atcgcgaaga gaggggagt aacagcggta  360
gaggcagtgc acgcctggcg caatgcgctc accggggccc cctgaacct gaccccggac  420
caagtggtgg ctatcgccag ccacgatggc ggcaagcaag cgctcgaaac ggtgcagcgg  480
ctgttgccgg tgctgtgcca ggaccatggc ctgaccccgg accaagtggt ggctatcgcc  540
agcaacggtg gcggcaagca agcgctcgaa acggtgcagc ggctgttgcc ggtgctgtgc  600
caggaccatg gcctgacccc ggaccaagtg gtggctatcg ccagcaacgg tggcggcaag  660
caagcgctcg aaacggtgca gcggctgttg ccggtgctgt gccaggacca tggcctgacc  720
ccggaccaag tggtggctat cgccagcaac attggcggca agcaagcgct cgaaacggtg  780
cagcggctgt tgccggtgct gtgccaggac catggcctga ctccggacca agtggtggct  840
atcgccagcc acgatggcgg caagcaagcg ctcgaaacgg tgcagcggct gttgccggtg  900
ctgtgccagg accatggcct gactccggac caagtggtgg ctatcgccag ccacgatggc  960
ggcaagcaag cgctcgaaac ggtgcagcgg ctgttgccgg tgctgtgcca ggaccatggc 1020
ctgactccgg accaagtggt ggctatcgcc agccacgatg gcggcaagca agcgctcgaa 1080
acggtgcagc ggctgttgcc ggtgctgtgc caggaccatg gcctgacccc ggaccaagtg 1140
gtggctatcg ccagcaacgg tggcggcaag caagcgctcg aaacggtgca gcggctgttg 1200
ccggtgctgt gccaggacca tggcctgacc ccggaccaag tggtggctat cgccagcaac 1260
ggtggcggca agcaagcgct cgaaacggtg cagcggctgt tgccggtgct gtgccaggac 1320
catggcctga ctccggacca agtggtggct atcgccagcc acgatggcgg caagcaagcg 1380
ctcgaaacgt gcagcggct gttgccggtg ctgtgccagg accatggcct gaccccggac 1440
caagtggtgg ctcgccag caacggtggc ggcaagcaag cgctcgaaac ggtgcagcgg 1500
ctgttgccgg tgctgtgcca ggaccatggc ctgactccgg accaagtggt ggctatcgcc 1560
agccacgatg gcggcaagca agcgctcgaa acggtgcagc ggctgttgcc ggtgctgtgc 1620
caggaccatg gcctgactcc ggaccaagtg gtggctatcg ccagccacga tggcggcaag 1680
caagcgctcg aaacggtgca gcggctgttg ccggtgctgt gccaggacca tggcctgact 1740
ccggaccaag tggtggctat cgccagccac gatggcggca agcaagcgct cgaaacggtg 1800
cagcggctgt tgccggtgct gtgccaggac catggcctga ccccggacca agtggtggct 1860
atcgccagca acattggcgg caagcaagcg ctcgaaacgg tgcagcggct gttgccggtg 1920
ctgtgccagg accatggcct gaccccggac caagtggtgg ctatcgccag caacggtggc 1980
ggcaagcaag cgctcgaaac ggtgcagcgg ctgttgccgg tgctgtgcca ggaccatggc 2040
ctgaccccgg accaagtggt ggctatcgcc agcaacggcg gcaagcaagc gctcgaatag 2100
agcattgtgg cccagctgag ccggcctgat ccgcgttgg ccgcgttgac caacgaccat 2160
ctggtggcgt tggcatgtct tggtggacgt cccgcgctcg atgcagtcaa aaagggtctg 2220
cctcatgctc ccgcattgat caaaagaacc aaccggcgga ttcccgagag aacttcccat 2280
cgagtcgcg gatcccaact agtcaaaagt gaactgaggg agaagaaatc tgaacttcgt 2340
cataaattga aatatgtgcc tcatgaatat attgaattaa ttgaaattgc cagaaattcc 2400
```

```
actcaggata gaattcttga aatgaaggta atggaatttt ttatgaaagt ttatggatat  2460
agaggtaaac atttgggtgg atcaaggaaa ccgacggag caatttatac tgtcggatct   2520
cctattgatt acggtgtgat cgtggatact aaagcttata gcggaggtta taatctgcca  2580
attggccaag cagatgaaat gcaacgtat gtcgaagaaa atcaaacacg aaacaaacat   2640
atcaaccta atgaatggtg gaaagtctat ccatctctat taacggaatt taagttttta   2700
tttgtgagtg gtcactttaa aggaaactac aaagctcagc ttacacgatt aaatcatatc   2760
actaattgta atggagctgt tcttagtgta gaagagcttt taattggtgg agaaatgatt   2820
aaagccggca cattaaacctt agaggaagtc agacggaaat taataacgg cgagataaac   2880
tttagatct                                                          2889

SEQ ID NO: 6              moltype = DNA   length = 2787
FEATURE                   Location/Qualifiers
source                    1..2787
                          mol_type = genomic DNA
                          organism = Homo sapiens
SEQUENCE: 6
gtggacttga ggacactcgg ttattcgcaa cagcaacagg agaaaatcaa gcctaaggtc   60
aggagcaccg tcgcgcaaca ccacgaggcg ctttgtgggc atggcttcac tcatgcgcat   120
attgtcgcgc tttcacagca ccctgcggcg cttgggacgg tggctgtcaa ataccaagat   180
atgattgcgg ccctgcccga agccacgcac gaggcaattg taggggtcgg taaacagtgg   240
tcgggagcgc gagcacttga ggccttgctg actgtggcgg gtgagcttag ggggcctccg   300
ctccagctcg acaccgggca gctgctgaag atcgcgaaga gaggggggagt aacagcagta   360
gaggcagtgc acgcctggcg caatgcgctc accggggccc ccctgaacct gaccccggac   420
caagtggtg ctatcgccag ccacgatggg ggcaagcaag cgctcgaaac ggtgcagcgg   480
ctgttgccga tgctgtgcca ggaccatggc ctgactccgg accaagtggt ggctatcgcc   540
agccacgatg gcggcaagca agcgctcgaa acggtgcagc ggctgttgcc ggtgctgtgc   600
caggaccatg gcctgactcc ggaccaagtg gtgctatcg ccagccacga tggcggcaag    660
caagcgctcg aaacggtgca gcggctgttg ccggtgctgt gccaggacca tggcctgacc   720
ccggaccaag tggtggctat cgccagcaac attggcggca agcaagcgct cgaaacggtg   780
cagcggctgt tgccggtgct gtgccaggac catggcctga ccccggacca agtggtggct   840
atcgccagca acattggcgg caagcaagcg ctcgaaacgg tgcagcggct gttgccggtg   900
ctgtgccagg accatggcct gaccccggac caagtggtgg ctatcgccag caacattggc   960
ggcaagcaag cgctcgaaac ggtgcagcgg ctgttgccgg tgctgtgcca ggaccatggc   1020
ctgaccccgg accaagtggt ggctatcgcc agcaacattg gcggcaagca agcgctcgaa   1080
acggtgcagc ggctgttgcc ggtgctgtgc caggaccatg gcctgacccc ggaccaagtg   1140
gtggctatcg ccagcaacgg tggcggcaag caagcgctcg aaacggtgca gcggctgttg   1200
ccggtgctgt gccaggacca tggcctgacc ccggaccaag tggtggctat cgccagcaac   1260
attggcggca agcaagcgct cgaaacggtg cagcggctgt tgccggtgct gtgccaggac   1320
catggcctga ccccggacca agtggtggct atcgccagca acggtggcgg caagcaagcg   1380
ctcgaaacgg tgcagcggct gttgccggtg ctgtgccagg accatggcct gaccccggac   1440
caagtggtgg ctatcgccag caacattggc ggcaagcaag cgctcgaaac ggtgcagcgg   1500
ctgttgccga tgctgtgcca ggaccatggc ctgaccccgg accaagtggt ggctatcgcc   1560
agcaacggtg gcggcaagca agcgctcgaa acggtgcagc ggctgttgcc ggtgctgtgc   1620
caggaccatg gcctgacccc ggaccaagtg gtgctatcg ccagcaacgg tggcggcaag    1680
caagcgctcg aaacggtgca gcggctgttg ccggtgctgt gccaggacca tggcctgacc   1740
ccggaccaag tggtggctat cgccagcaac ggtggcggca agcaagcgct cgaaacggtg   1800
cagcggctgt tgccggtgct gtgccaggac catggcctga ccccggacca agtggtggct   1860
atcgccagca acattggcgg caagcaagcg ctcgaaacgg tgcagcggct gttgccggtg   1920
ctgtgccagg accatggcct gaccccggac caagtggtgg ctatcgccag caacggtggc   1980
ggcaagcaag cgctcgaaag cattgtggcc cagctgagcc ggcctgatcc ggcgttggcc   2040
ggttgacca acgaccatct ggtggcgttg gcatgtcttg gtggacgtcc cgctcgat     2100
gcagtcaaaa agggtctgcc tcatgctccc gcattgatca aaagaaccaa ccggcggatt   2160
cccgagagaa cttcccatcg agtcgcggga tccaactag tcaaaagtga actgaaggag   2220
aagaaatctg aacttcgtca taaattgaaa tatgtgcctc atgaatatat tgaattaatt   2280
gaaattgcca gaaattccac tcaggataga attcttgaaa tgaaggtaat ggaatttttt   2340
atgaaagttt atggatatag aggtaaacat ttgggtggat caaggaaacc ggacggagca   2400
atttatactg tcggatctcc tattgattac ggtgtgatcg tggatactaa agcttatagc   2460
ggaggttata atctgccaat tggccaagca gatgaaatgc aacgatatgt cgaagaaaat   2520
caaacacgaa acaaacatat caaccctaat gaatggtgga aagtctatcc atctctgta    2580
acggaattta gttttttatt tgtgagtggt cactttaaag gaaactacaa agctcagctt   2640
acacgattaa atcatatcac taattgtaat ggagctgttc ttagtgtaga agagctttta   2700
attggtggag aaatgattaa agccggcaca ttaaccttag aggaagtcag acggaaattt   2760
aataacggcg agataaactt tagatct                                      2787

SEQ ID NO: 7              moltype = AA   length = 564
FEATURE                   Location/Qualifiers
source                    1..564
                          mol_type = protein
                          organism = Homo sapiens
SEQUENCE: 7
LTPDQVVAIA SHDGGKQALE TVQRLLPVLC QDHGLTPDQV VAIASNGGGK QALETVQRLL   60
PVLCQDHGLT PDQVVAIASN GGGKQALETV QRLLPVLCQD HGLTPDQVVA IASNIGGKQA   120
LETVQRLLPV LCQDHGLTPD QVVAIASHDG GKQALETVQR LLPVLCQDHG LTPDQVVAIA   180
SHDGGKQALE TVQRLLPVLC QDHGLTPDQV VAIASHDGGK QALETVQRLL PVLCQDHGLT   240
PDQVVAIASN GGGKQALETV QRLLPVLCQD HGLTPDQVVA IASNGGGKQA LETVQRLLPV   300
LCQDHGLTPD QVVAIASHDG GKQALETVQR LLPVLCQDHG LTPDQVVAIA SNGGGKQALE   360
TVQRLLPVLC QDHGLTPDQV VAIASHDGGK QALETVQRLL PVLCQDHGLT PDQVVAIASH   420
DGGKQALETV QRLLPVLCQD HGLTPDQVVA IASHDGGKQA LETVQRLLPV LCQDHGLTPD   480
QVVAIASNIG GKQALETVQR LLPVLCQDHG LTPDQVVAIA SNGGGKQALE TVQRLLPVLC   540
```

| QDHGLTPDQV VAIASNGGGK QALE | 564 |

```
SEQ ID NO: 8              moltype = AA  length = 963
FEATURE                   Location/Qualifiers
source                    1..963
                          mol_type = protein
                          organism = Homo sapiens
SEQUENCE: 8
VDLRTLGYSQ QQQEKIKPKV RSTVAQHHEA LVGHGFTHAH IVALSQHPAA LGTVAVKYQD    60
MIAALPEATH EAIVGVGKQW SGARALEALL TVAGELRGPP LQLDTGQLLK IAKRGGVTAV   120
EAVHAWRNAL TGAPLNLTPD QVVAIASHDG KQALETVQR LLPVLCQDHG LTPDQVVAIA   180
SNGGGKQALE TVQRLLPVLC QDHGLTPDQV VAIASNGGGK QALETVQRLL PVLCQDHGLT   240
PDQVVAIASN IGGKQALETV QRLLPVLCQD HGLTPDQVVA IASHDGGKQA LETVQRLLPV   300
LCQDHGLTPD QVVAIASHDG GKQALETVQR LLPVLCQDHG LTPDQVVAIA SHDGGKQALE   360
TVQRLLPVLC QDHGLTPDQV VAIASNGGGK QALETVQRLL PVLCQDHGLT PDQVVAIASN   420
GGGKQALETV QRLLPVLCQD HGLTPDQVVA IASHDGGKQA LETVQRLLPV LCQDHGLTPD   480
QVVAIASNGG GKQALETVQR LLPVLCQDHG LTPDQVVAIA SHDGGKQALE TVQRLLPVLC   540
QDHGLTPDQV VAIASHDGGK QALETVQRLL PVLCQDHGLT PDQVVAIASH DGGKQALETV   600
QRLLPVLCQD HGLTPDQVVA IASNIGGKQA LETVQRLLPV LCQDHGLTPD QVVAIASNGG   660
GKQALETVQR LLPVLCQDHG LTPDQVVAIA SNGGGKQALE SIVAQLSRPD PALAALTNDH   720
LVALACLGGR PALDAVKKGL PHAPALIKRT NRRIPERTSH RVAGSQLVKS ELEEKKSELR   780
HKLKYVPHEY IELIEIARNS TQDRILEMKV MEFFMKVYGY RGKHLGGSRK PDGAIYTVGS   840
PIDYGVIVDT KAYSGGYNLP IGQADEMQRY VEENQTRNKH INPNEWWKVY PSSVTEFKFL   900
FVSGHFKGNY KAQLTRLNHI TNCNGAVLSV EELLIGGEMI KAGTLTLEEV RRKFNNGEIN   960
FRS                                                                963

SEQ ID NO: 9              moltype = DNA  length = 3006
FEATURE                   Location/Qualifiers
source                    1..3006
                          mol_type = genomic DNA
                          organism = Homo sapiens
SEQUENCE: 9
atggactaca aagaccatga cggtgattat aaagatcatg acatcgatta caaggatgac    60
gatgacaaga tggcccccaa gaagaagagg aaggtgggca tccacgggt acctatggtg   120
gacttgagga cactcggtta ttcgcaacag caacaggaaa aaatcaagcc taaggtcagg   180
agcaccgtcg cgcaacacca cgaggcgctt gtgggcatg gcttcactca tgcgcatatt   240
gtcgcgcttt cacagcaccc tgcggcgctt gggacggtgg ctgtcaaata ccaagatatg   300
attgcggccc tgcccgaagc cacgcacgag caattgtag gggtcggtaa acagtggtcg   360
ggagcgcgag cacttgaggc cttgctgact gtggcggagt agcttagggg gcctccgctc   420
cagctcgaca ccgggcagct gctgaagatc gcgaagagag ggggagtaac agcggtagag   480
gcagtgcacg cctggcgcaa tgcgctcacc ggggccccc tgaacctgac cccggaccaa   540
gtggtggcta tcgccagcca cgatggcggc aagcaagcgc tcgaaacggt gcagcggctg   600
ttgccggtgc tgtgccagga ccatggcctg accccgacc aagtgtggc tatcgccagc   660
aacggtggcg gcaagcaagc gctcgaaacg gtgcagcggc tgttgccggt gctgtgccag   720
gaccatggcc tgaccccgga ccaagtggtg gctatcgcca gcaacggtgg cggcaagcaa   780
gcgctcgaaa cggtgcagcg gctgttgccg gtgctgtgcc aggaccatgg cctgaccccg   840
gaccaagtgg tggctatcgc cagcaacatt ggcggcaagc aagcgctcga aacggtgcag   900
cggctgttgc cggtgctgtg ccaggaccat ggcctgactc cggaccaagt ggtggctatc   960
gccagccacg atgcggcaa gcaagcgctc gaaacggtgc agcggctgtt gccggtgctg  1020
tgccaggacc atggcctgac tccggaccaa gtggtggcta tcgccagcca cgatggcggc  1080
aagcaagcgc tcgaaacggt gcagcggctg ttgccggtgc tgtgccagga ccatggcctg  1140
actccggacc aagtggtggc tatcgccagc cacgatggcg gcaagcaagc gctcgaaacg  1200
gtgcagcggc tgttgccggt gctgtgccag gaccatggcc tgaccccgga ccaagtggtg  1260
gctatcgcca gcaacggtgg cggcaagcaa gcgctcgaaa cggtgcagcg gctgttgccg  1320
gtgctgtgcc aggaccatgg cctgaccccg gaccaagtgg tggctatcgc cagcaacggt  1380
ggcggcaagc aagcgctcga aacggtgcag cggctgttgc cggtgctgtg ccaggaccat  1440
ggcctgactc cggaccaagt ggtggctatc gccagccacg atgcggcaa gcaagcgctc  1500
gaaacggtgc agcggctgtt gccggtgctg tgccaggacc atggcctgac cccggaccaa  1560
gtggtggcta tcgccagcaa cggtggcggc aagcaagcgc tcgaaacggt gcagcggctg  1620
ttgccggtgc tgtgccagga ccatggcctg actccggacc aagtggtggc tatcgccagc  1680
cacgatggcg gcaagcaagc gctcgaaacg gtgcagcggc tgttgccggt gctgtgccag  1740
gaccatggcc tgactccgga ccaagtggtg gctatcgcca gccacgatgg cggcaagcaa  1800
gcgctcgaaa cggtgcagcg gctgttgccg gtgctgtgcc aggaccatgg cctgactccg  1860
gaccaagtgg tggctatcgc cagccacgat gcggcaagc aagcgctcga aacggtgcag  1920
cggctgttgc cggtgctgtg ccaggaccat ggcctgaccc cggaccaagt ggtggctatc  1980
gccagcaaca ttggcggcaa gcaagcgctc gaaacggtgc agcggctgtt gccggtgctg  2040
tgccaggacc atggcctgac cccggaccaa gtggtggcta tcgccagcaa cggtggcggc  2100
aagcaagcgc tcgaaacggt gcagcggctg ttgccggtgc tgtgccagga ccatggcctg  2160
accccggacc aagtggtggc tatcgccagc aacggtggca gcaagcaag gtcgaaagc  2220
attgtggccc agctgagccg gcctgatccg gcgttggccg cgttgaccaa cgaccatctg  2280
gtggcgttgg catgtcttgg tggacgtccc gcgctcgatg cagtcaaaaa gggtctgcct  2340
catgctcccg cattgatcaa aagaaccaac ggcggattc cgagagaac ttcccatcga  2400
gtcgcgggat cccaactagt caaaagtgaa ctggaggaga gaaatctga acttcgtcat  2460
aaattgcaaa atgtcgctca tgaatatatt gaattcgtta aattgcgaaa aaattccact  2520
caggatagaa ttcttgaaat gaaggtaatg gaatttttta tgaaagttta tggatataga  2580
ggtaaacatt tgggtggatc aaggaaaccg acggagcaa tttatactgt cggatctcct  2640
attgattacg gtgtgatcgt ggatactaaa gcttatagcg gaggttataa tctgccaatt  2700
ggccaagcag atgaaatgca acgatatgtc gaagaaaatc aaacacgaaa caacatatc  2760
aaccctaatg aatggtggaa agtctatcca tcttctgtaa cggaatttaa gttttttattt  2820
```

```
gtgagtggtc actttaaagg aaactacaaa gctcagctta cacgattaaa tcatatcact    2880
aattgtaatg gagctgttct tagtgtagaa gagcttttaa ttggtggaga aatgattaaa    2940
gccggcacat taaccttaga ggaagtcaga cggaaattta ataacggcga gataaacttt    3000
agatct                                                              3006

SEQ ID NO: 10           moltype = AA  length = 530
FEATURE                 Location/Qualifiers
source                  1..530
                        mol_type = protein
                        organism = Homo sapiens
SEQUENCE: 10
LTPDQVVAIA SHDGGKQALE TVQRLLPVLC QDHGLTPDQV VAIASHDGGK QALETVQRLL     60
PVLCQDHGLT PDQVVAIASH DGGKQALETV QRLLPVLCQD HGLTPDQVVA IASNIGGKQA    120
LETVQRLLPV LCQDHGLTPD QVVAIASNIG GKQALETVQR LLPVLCQDHG LTPDQVVAIA    180
SNIGGKQALE TVQRLLPVLC QDHGLTPDQV VAIASNIGGK QALETVQRLL PVLCQDHGLT    240
PDQVVAIASN GGGKQALETV QRLLPVLCQD HGLTPDQVVA IASNIGGKQA LETVQRLLPV    300
LCQDHGLTPD QVVAIASNGG GKQALETVQR LLPVLCQDHG LTPDQVVAIA SNIGGKQALE    360
TVQRLLPVLC QDHGLTPDQV VAIASNGGGK QALETVQRLL PVLCQDHGLT PDQVVAIASN    420
GGGKQALETV QRLLPVLCQD HGLTPDQVVA IASNGGGKQA LETVQRLLPV LCQDHGLTPD    480
QVVAIASNIG GKQALETVQR LLPVLCQDHG LTPDQVVAIA SNGGGKQALE                530

SEQ ID NO: 11           moltype = AA  length = 929
FEATURE                 Location/Qualifiers
source                  1..929
                        mol_type = protein
                        organism = Homo sapiens
SEQUENCE: 11
VDLRTLGYSQ QQQEKIKPKV RSTVAQHHEA LVGHGFTHAH IVALSQHPAA LGTVAVKYQD     60
MIAALPEATH EAIVGVGKQW SGARALEALL TVAGELRGPP LQLDTGQLLK IAKRGGVTAV    120
EAVHAWRNAL TGAPLNLTPD QVVAIASHDG KQALETVQRL LPVLCQDHGL TPDQVVAIAS    180
SHDGGKQALE TVQRLLPVLC QDHGLTPDQV VAIASHDGGK QALETVQRLL PVLCQDHGLT    240
PDQVVAIASN IGGKQALETV QRLLPVLCQD HGLTPDQVVA IASNIGGKQA LETVQRLLPV    300
LCQDHGLTPD QVVAIASNIG GKQALETVQR LLPVLCQDHG LTPDQVVAIA SNIGGKQALE    360
TVQRLLPVLC QDHGLTPDQV VAIASNGGGK QALETVQRLL PVLCQDHGLT PDQVVAIASN    420
IGGKQALETV QRLLPVLCQD HGLTPDQVVA IASNGGGKQA LETVQRLLPV LCQDHGLTPD    480
QVVAIASNIG GKQALETVQR LLPVLCQDHG LTPDQVVAIA SNGGGKQALE TVQRLLPVLC    540
QDHGLTPDQV VAIASNGGGK QALETVQRLL PVLCQDHGLT PDQVVAIASN GGGKQALETV    600
QRLLPVLCQD HGLTPDQVVA IASNIGGKQA LETVQRLLPV LCQDHGLTPD QVVAIASNGG    660
GKQALESIVA QLSRPDPALA ALTNDHLVAL ACLGGRPALD AVKKGLPHAP ALIKRTNRRI    720
PERTSHRVAG SQLVKSELEE KKSELRHKLK YVPHEYIELI EIARNSTQDR ILEMKVMEFF    780
MKVYGYRGKH LGGSRKPDGA IYTVGSPIDY GVIVDTKAYS GGYNLPIGQA DEMQRYVEEN    840
QTRNKHINPN EWWKVYPSSV TEFKFLFVSG HFKGNYKAQL TRLNHITNCN GAVLSVEELL    900
IGGEMIKAGT LTLEEVRRKF NNGEINFRS                                     929

SEQ ID NO: 12           moltype = DNA  length = 2904
FEATURE                 Location/Qualifiers
source                  1..2904
                        mol_type = genomic DNA
                        organism = Homo sapiens
SEQUENCE: 12
atggactaca aagaccatga cggtgattat aaagatcatg acatcgatta caaggatgac     60
gatgacaaga tggcccccaa gaagaagagg aaggtgggca tccacggggt acctatggtg    120
gacttgagga cactcggtta ttcgcaacag caacaggaga aaatcaagcc taaggtcagg    180
agcaccgtcg cgcaacacca cgaggcgctt gtggggcatg gcttcactca tgcgcatatt    240
gtcgcgcttt cacagcaccc tgcggcgctt gggacgtggg ctgtcaaata ccaagatatg    300
attgcggccc tgcccgaagc cacgcacgag gcaattgtag gggtcggtaa acagtggtcg    360
ggagcgcgag cacttgaggc cttgctgact gtggcgggtg agcttagggg gcctccgctc    420
cagctcgaca ccgggcagct gctgaagatc gcgaagagag ggggagtaac agcggtagag    480
gcagtgcacg cctggcgcaa tgcgctcacc ggggccccca tgaacctgac cccggaccaa    540
gtggtggcta tcgccagcca cgatggcggg aagcaagcgc tcgaaacgtc gcagcggctg    600
ttgccggtgc tgtgccagga ccatggcctg actccggacc aagtggtggc tatcgccagc    660
cacgatggcg gcaagcaagc gctcgaaacg gtgcagcggc tgttgccggt gctgtgccag    720
gaccatggcc tgactccgga ccaagtggtg gctatcgcca gccacgatgg cggcaagcaa    780
gcgctcgaaa cggtgcagcg gctgttgccg gtgctgtgcc aggaccatgg cctgaccccg    840
gaccaagtgg tggctatcgc cagcaacatt ggcggcaagc aagcgctcga aacggtgcag    900
cggctgttgc cggtgctgtg ccaggaccat ggcctgaccc ggaccaagt ggtggctatc    960
gccagcaaca ttggcggcaa gcaagcgctc gaaacggtgc agcggctgtt gccggtgctg   1020
tgccaggacc atggcctgac cccggaccaa gtggtggcta tcgccagcaa cattggcggc   1080
aagcaagcgc tcgaaacggt gcagcggctg ttgccggtgc tgtgccagga ccatggcggc   1140
acccggacc aagtggtggc tatcgccagc aacattggcg gcaagcaagc gctcgaaacg   1200
gtgcagcggc tgttgccggt gctgtgccag gaccatggcc tgaccccgga ccaagtggtg   1260
gctatcgcca gcaacggtgg cggcaagcaa gcgctcgaaa cggtgcagcg gctgttgccg   1320
gtgctgtgcc aggaccatgg cctgacccog gaccaagtgg tggctatcgc cagcaacatt   1380
ggcggcaagc aagcgctcga aacggtgcag cggctgttgc cggtgctgtg ccaggaccat   1440
ggcctgaccc ggaccaagt ggtggctatc gccagcaacg gtggcggcaa gcaagcgctc   1500
gaaacggtgc agcggctgtt gccggtgctg tgccaggacc atggcctgac cccggaccaa   1560
gtggtggcta tcgccagcaa cattggcggc aagcaagcgc tcgaaacggt gcagcggctg   1620
ttgccggtgc tgtgccagga ccatggcctg accccggacc aagtggtggc tatcgccagc   1680
aacggtggcg gcaagcaagc gctcgaaacg gtgcagcggc tgttgccggt gctgtgccag   1740
```

```
gaccatggcc tgaccccgga ccaagtggtg gctatcgcca gcaacggtgg cggcaagcaa      1800
gcgctcgaaa cggtgcagcg gctgttgccg gtgctgtgcc aggaccatgg cctgaccccg      1860
gaccaagtgg tggctatcgc cagcaacggt ggcggcaagc aagcgctcga acggtgcag       1920
cggctgttgc cggtgctgtg ccaggaccat ggcctgaccc cggaccaagt ggtggctatc      1980
gccagcaaca ttggcggcaa gcaagcgctc gaaacggtgc agcggctgtt gccggtgctg      2040
tgccaggacc atggcctgac cccgaccaa gtggtggcta tcgccagcaa cggtggcggc       2100
aagcaagcgc tcgaaagcat tgtgcccag ctgagccggc ctgatccggc gttggccgcg       2160
ttgaccaacg accatctggt ggcgttggca tgtcttggtg acgtccgc gctcgatgca        2220
gtcaaaaagg gtctgcctca tgctcccga ttgatcaaaa gaaccaaccg gcggattcc        2280
gagagaactt cccatcgagt cgcgggatcc caactagtca aaagtgaact ggaggagaag      2340
aaatctgaac ttcgtcataa attgaaatat gtgcctcatg aatatattga attaattgaa      2400
attgccagaa attccactca ggatagaatt cttgaaatga aggtaatgga attttttatg      2460
aaagtttatg gatatagagg taaacatttg ggtggatcaa ggaaaccgga cggagcaatt      2520
tatactgtcg gatctcctat tgattacggt gtgatcggtg atactaaagc ttatagcgga      2580
ggttataatc tgccaattgg ccaagcagat gaaatgcaac gatatgtcga agaaaatcaa      2640
acacgaaaca aacatatcaa ccctaatgaa tggtggaaag tctatccatc ttctgtaacg      2700
gaatttaagt ttttatttgt gagtggtcac tttaaaggaa actacaaagc tcagcttaca      2760
cgattaaatc atatcactaa ttgtaatgga gctgttctta gtgtagaaga gcttttaatt      2820
ggtggagaaa tgattaaagc cggcacatta accttagagg aagtcagacg gaaatttaat      2880
aacggcgaga taaactttag atct                                             2904

SEQ ID NO: 13            moltype = AA   length = 199
FEATURE                  Location/Qualifiers
source                   1..199
                         mol_type = protein
                         organism = Homo sapiens
SEQUENCE: 13
SQLVKSELEE KKSELRHKLK YVPHEYIELI EIARNSTQDR ILEMKVMEFF MKVYGYRGKH       60
LGGSRKPDGA IYTVGSPIDY GVIVDTKAYS GGYNLPIGQA DEMQRYVEEN QTRNKHINPN      120
EWWKVYPSSV TEFKFLFVSG HFKGNYKAQL TRLNHITNCN GAVLSVEELL IGGEMIKAGT      180
LTEEVRRKF NNGEINFRS                                                    199

SEQ ID NO: 14            moltype = DNA   length = 597
FEATURE                  Location/Qualifiers
source                   1..597
                         mol_type = genomic DNA
                         organism = Homo sapiens
SEQUENCE: 14
tcccaactag tcaaaagtga actggaggag aagaaatctg aacttcgtca taaattgaaa       60
tatgtgcctc atgaatatat tgaattaatt gaaattgcca gaaattccac tcaggataga      120
attcttgaaa tgaaggtaat ggattttttt atgaaagttt atggatatag aggtaaacat      180
ttgggtggat caaggaaacc ggacggagca atttatactg tcggatctcc tattgattac      240
ggtgtgatcg tggatactaa agcttatagc ggaggttata atctgccaat tggccaagca      300
gatgaaatgc aacgatatgt cgaagaaaat caaacacgaa acaaacatat caaccctaat      360
gaatggtgga agtctatcc atcttctgta acggaattta gttttttatt tgtgagtggt      420
cactttaaag gaaactacaa agctcagctt acacgattaa atcatatcac taattgtaat      480
ggagctgttc ttagtgtaga gagcttttta attggtggag aaatgattaa agccggcaca      540
ttaaccttag aggaagtcag acggaaattt aataacggcg agataaactt tagatct        597

SEQ ID NO: 15            moltype = DNA   length = 21
FEATURE                  Location/Qualifiers
source                   1..21
                         mol_type = genomic DNA
                         organism = Homo sapiens
SEQUENCE: 15
cccaagaaga agaggaaggt g                                                 21

SEQ ID NO: 16            moltype = AA   length = 7
FEATURE                  Location/Qualifiers
source                   1..7
                         mol_type = protein
                         organism = Homo sapiens
SEQUENCE: 16
PKKKRKV                                                                  7

SEQ ID NO: 17            moltype = DNA   length = 69
FEATURE                  Location/Qualifiers
source                   1..69
                         mol_type = genomic DNA
                         organism = Homo sapiens
SEQUENCE: 17
atggactaca aagaccatga cggtgattat aaagatcatg acatcgatta caaggatgac       60
gatgacaag                                                               69

SEQ ID NO: 18            moltype = AA   length = 23
FEATURE                  Location/Qualifiers
source                   1..23
                         mol_type = protein
                         organism = Homo sapiens
```

```
SEQUENCE: 18
MDYKDHDGDY KDHDIDYKDD DDK                                              23

SEQ ID NO: 19            moltype = DNA  length = 49
FEATURE                  Location/Qualifiers
source                   1..49
                         mol_type = genomic DNA
                         organism = Homo sapiens
SEQUENCE: 19
cttacccttc tcccatttcc tcatccttcc aacataaata tattttggg                  49

SEQ ID NO: 20            moltype = DNA  length = 20
FEATURE                  Location/Qualifiers
source                   1..20
                         mol_type = genomic DNA
                         organism = Homo sapiens
SEQUENCE: 20
ctgccgtctc tctcctgagt                                                  20

SEQ ID NO: 21            moltype = DNA  length = 20
FEATURE                  Location/Qualifiers
source                   1..20
                         mol_type = genomic DNA
                         organism = Homo sapiens
SEQUENCE: 21
gtgggcttgt actcggtcat                                                  20

SEQ ID NO: 22            moltype = DNA  length = 21
FEATURE                  Location/Qualifiers
misc_feature             1..21
                         note = Synthetic
source                   1..21
                         mol_type = other DNA
                         organism = synthetic construct
SEQUENCE: 22
gctttctgtc tgcagcttgt g                                                21

SEQ ID NO: 23            moltype = DNA  length = 10
FEATURE                  Location/Qualifiers
misc_feature             1..10
                         note = Synthetic
source                   1..10
                         mol_type = other DNA
                         organism = synthetic construct
SEQUENCE: 23
acagtggggc                                                             10

SEQ ID NO: 24            moltype =      length =
SEQUENCE: 24
000

SEQ ID NO: 25            moltype =      length =
SEQUENCE: 25
000

SEQ ID NO: 26            moltype = DNA  length = 16
FEATURE                  Location/Qualifiers
misc_feature             1..16
                         note = Synthetic
source                   1..16
                         mol_type = other DNA
                         organism = synthetic construct
SEQUENCE: 26
tctgctcttc agactg                                                      16

SEQ ID NO: 27            moltype = DNA  length = 19
FEATURE                  Location/Qualifiers
misc_feature             1..19
                         note = Synthetic
source                   1..19
                         mol_type = other DNA
                         organism = synthetic construct
SEQUENCE: 27
tggcgagacc agcaggaga                                                   19

SEQ ID NO: 28            moltype =      length =
SEQUENCE: 28
000
```

```
SEQ ID NO: 29            moltype = DNA  length = 10
FEATURE                  Location/Qualifiers
misc_feature             1..10
                         note = Synthetic
source                   1..10
                         mol_type = other DNA
                         organism = synthetic construct
SEQUENCE: 29
tcctcatcct                                                              10

SEQ ID NO: 30            moltype = DNA  length = 16
FEATURE                  Location/Qualifiers
misc_feature             1..16
                         note = Synthetic
source                   1..16
                         mol_type = other DNA
                         organism = synthetic construct
SEQUENCE: 30
acagagccgt aaagtg                                                       16

SEQ ID NO: 31            moltype = DNA  length = 21
FEATURE                  Location/Qualifiers
misc_feature             1..21
                         note = Synthetic
source                   1..21
                         mol_type = other DNA
                         organism = synthetic construct
SEQUENCE: 31
cagcgtcata ttggtcctat g                                                 21

SEQ ID NO: 32            moltype = DNA  length = 16
FEATURE                  Location/Qualifiers
misc_feature             1..16
                         note = Synthetic
source                   1..16
                         mol_type = other DNA
                         organism = synthetic construct
SEQUENCE: 32
cacccatcga tggaag                                                       16

SEQ ID NO: 33            moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 33
ctgctagcat ggtcttca                                                     18

SEQ ID NO: 34            moltype =   length =
SEQUENCE: 34
000

SEQ ID NO: 35            moltype = DNA  length = 17
FEATURE                  Location/Qualifiers
misc_feature             1..17
                         note = Synthetic
source                   1..17
                         mol_type = other DNA
                         organism = synthetic construct
SEQUENCE: 35
taaccctgtt ttagtgc                                                      17

SEQ ID NO: 36            moltype = DNA  length = 21
FEATURE                  Location/Qualifiers
misc_feature             1..21
                         note = Synthetic
source                   1..21
                         mol_type = other DNA
                         organism = synthetic construct
SEQUENCE: 36
cagcgtcata ttggtcctat g                                                 21

SEQ ID NO: 37            moltype = DNA  length = 15
FEATURE                  Location/Qualifiers
misc_feature             1..15
                         note = Synthetic
source                   1..15
```

-continued

```
                    mol_type = other DNA
                    organism = synthetic construct
SEQUENCE: 37
tgtgatcgat ggaag                                                15

SEQ ID NO: 38       moltype =    length =
SEQUENCE: 38
000

SEQ ID NO: 39       moltype = DNA  length = 17
FEATURE             Location/Qualifiers
misc_feature        1..17
                    note = Synthetic
source              1..17
                    mol_type = other DNA
                    organism = synthetic construct
SEQUENCE: 39
tgctgtgtca taccagg                                              17
```